(12) United States Patent
Oetter et al.

(10) Patent No.: US 7,872,067 B2
(45) Date of Patent: Jan. 18, 2011

(54) AMPHIPHILIC POLYMER COMPOSITIONS AND THEIR USE

(75) Inventors: Günter Oetter, Frankenthal (DE); Christian Krüger, Saulheim (DE); Harald Köhle, Bobenheim (DE); Maria Scherer, Godramstein (DE); Norbert Wagner, Mutterstadt (DE); Matthias Bratz, Maxdorf (DE); Rainer Berghaus, Speyer (DE); Richard van Gelder, Speyer (NL)

(73) Assignee: BASF Aktiengesellschaft, Ludwigshafen (DE)

( * ) Notice: Subject to any disclaimer, the term of this patent is extended or adjusted under 35 U.S.C. 154(b) by 154 days.

(21) Appl. No.: 11/628,609

(22) PCT Filed: Jun. 7, 2005

(86) PCT No.: PCT/EP2005/006106

§ 371 (c)(1), (2), (4) Date: Dec. 5, 2006

(87) PCT Pub. No.: WO2005/121201

PCT Pub. Date: Dec. 22, 2005

(65) Prior Publication Data

US 2008/0287593 A1 Nov. 20, 2008

(30) Foreign Application Priority Data

Jun. 8, 2004 (DE) ........................ 10 2004 027 835

(51) Int. Cl.
*C08G 18/08* (2006.01)
(52) U.S. Cl. ........................ 524/507; 525/377; 525/187; 524/502
(58) Field of Classification Search ................. 524/507, 524/502; 525/187, 377
See application file for complete search history.

(56) References Cited

U.S. PATENT DOCUMENTS

| | | | |
|---|---|---|---|
| 4,795,796 A | 1/1989 | Haubennestel et al. | |
| 4,888,389 A | 12/1989 | Kennedy et al. | |
| 4,942,213 A | 7/1990 | Haubennestel et al. | |
| 5,489,389 A * | 2/1996 | Ritter et al. | 252/8.57 |
| 5,556,918 A * | 9/1996 | Brodt et al. | 525/131 |
| 5,756,637 A | 5/1998 | Brodt et al. | |
| 5,838,863 A | 11/1998 | Fujiura et al. | |
| 6,075,107 A * | 6/2000 | Kothrade et al. | 526/264 |
| 6,132,880 A | 10/2000 | Weingart et al. | |
| 6,150,468 A * | 11/2000 | Schoenberg et al. | 525/222 |
| 6,489,382 B1 * | 12/2002 | Giesecke et al. | 524/89 |
| 6,506,899 B1 * | 1/2003 | Simms | 544/222 |
| 6,616,946 B1 | 9/2003 | Meier et al. | |
| 6,680,355 B1 | 1/2004 | Weingart et al. | |
| 2003/0009004 A1 | 1/2003 | Nam et al. | |
| 2003/0050385 A1 | 3/2003 | Probst et al. | |
| 2003/0060514 A1 * | 3/2003 | Aven | 514/679 |
| 2003/0153001 A1 * | 8/2003 | Soane et al. | 435/7.1 |
| 2003/0157170 A1 | 8/2003 | Liggins et al. | |
| 2005/0090402 A1 * | 4/2005 | Dieing et al. | 504/361 |
| 2006/0229209 A1 * | 10/2006 | Chrisstoffels et al. | 504/361 |
| 2007/0122436 A1 | 5/2007 | Koltzenburg et al. | |

(Continued)

FOREIGN PATENT DOCUMENTS

| | | |
|---|---|---|
| DE | 197 34 893 | 2/1999 |
| EP | 270 126 | 6/1988 |
| EP | 0 318 999 | 6/1989 |
| EP | 0 742 238 | 11/1996 |

(Continued)

*Primary Examiner*—Mark Eashoo
*Assistant Examiner*—Jane L Stanley
(74) *Attorney, Agent, or Firm*—Brinks Hofer Gilson & Lione

(57) ABSTRACT

The present invention relates to amphiphilic polymer compositions, to a process for their preparation and to their use for preparing aqueous active compound compositions of water-insoluble active compounds, in particular active compounds for crop protection.

The amphiphilic polymer compositions can be obtained by reacting
a) at least one hydrophobic polymer P1 which carries functional groups $R^1$ which are reactive toward isocyanate groups and which is constructed of ethylenically unsaturated monomers M1, comprising:
   a1) at least 10% by weight, based on the total amount of monomers M1, of monomers M1a of the formula I

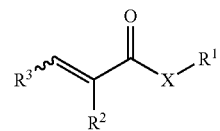

(I)

in which X is oxygen or a group $N-R^4$;
$R^1$, $R^2$, $R^3$ and $R^4$ are as defined in the claims and the description;
   a2) up to 90% by weight, based on the total amount of monomers M1, of neutral monoethylenically unsaturated monomers M1b whose solubility in water at 25° C. is less than 50 g/l and which are different from the monomers M1a; and
   a3) up to 30% by weight, based on the total amount of monomers M1, of ethylenically unsaturated monomers M1c which are different from the monomers M1a and M1b,
b) at least one hydrophilic polymer P2 which carries functional groups $R^2$ which are reactive toward isocyanate groups,
c) with at least one compound V which contains isocyanate groups and, with respect to the isocyanate groups, has a functionality of at least 1.5.

22 Claims, No Drawings

U.S. PATENT DOCUMENTS

| | | | |
|---|---|---|---|
| 2008/0041546 A1* | 2/2008 | Schmid et al. | 162/164.6 |
| 2008/0089853 A1* | 4/2008 | Nguyen-Kim et al. | 424/61 |
| 2008/0167189 A1* | 7/2008 | Oetter et al. | 504/360 |
| 2008/0199416 A1* | 8/2008 | Nguyen Kim et al. | 424/70.11 |
| 2009/0041813 A1* | 2/2009 | Bouillo et al. | 424/401 |
| 2009/0074692 A1* | 3/2009 | Biganska et al. | 424/70.2 |
| 2010/0048655 A1* | 2/2010 | Koltzenburg et al. | 514/383 |

FOREIGN PATENT DOCUMENTS

| | | |
|---|---|---|
| EP | 0 790 265 | 8/1997 |
| EP | 1 160 265 A1 * | 12/2001 |
| EP | 1 270 619 | 1/2003 |
| WO | WO 96/01054 | 1/1996 |
| WO | WO 98/51723 | 11/1998 |
| WO | WO 00/17250 | 3/2000 |
| WO | WO 01/10923 | 2/2001 |
| WO | WO 02/082900 | 12/2002 |
| WO | WO 2008/040786 | 4/2008 |

* cited by examiner

AMPHIPHILIC POLYMER COMPOSITIONS AND THEIR USE

The present invention relates to amphiphilic polymer compositions, to a process for their preparation and to their use for preparing aqueous active compound compositions of water-insoluble active compounds, in particular of active compounds for crop protection.

Active compounds, i.e. substances capable of exerting a physiological action even at low concentration, are frequently formulated in the form of aqueous active compound preparations. Thus, for example, active compounds used in crop protection for controlling pests, i.e. insecticides, fungicides and herbicides, but also growth regulators, are frequent formulated and sold as aqueous concentrates which, prior to their application, are diluted to the desired application concentration by adding a large amount of water ("spray liquor"). Aqueous active compound preparations have also proven themselves to be useful for pharmaceutically and cosmetically active substances and for food additives, for example vitamins, provitamins, etc. The same applies to the formulation of effect substances, i.e. low-molecular-weight compounds which exact a defined technical action even at a low application rate, for example colorants and UV stabilizers.

A general problem in the case of aqueous active compound preparations is the generally poor solubility of the active compounds in water, which is frequently less than 10 g/l at 23° C./1013 mbar. Accordingly, aqueous formulations of such active compounds are heterogeneous systems where the active compound is present as an emulsified and/or dispersed phase in a continuous aqueous phase. For stabilizing these systems, which are metastable per se, it is customary to employ emulsifiers or dispersants. However, their stabilizing action is frequently unsatisfactory, so that the active compound may separate out, for example cream or sediment, in particular if the aqueous formulation is stored for a relatively long period of time at elevated temperature and/or at highly variable temperatures or close to freezing point. This problem is particularly pronounced if the active compound has a tendency to crystallize.

Organic solvents, too, are frequently used for preparing aqueous formulations of water-insoluble active compounds. Thus, water-miscible solvents are frequently used as solubilizers, i.e. to increase the solubility of the active compound or effect substance in the aqueous phase. Water-immiscible solvents, in turn, serve to convert an active compound which is solid at the application temperature into a liquid phase which can then be emulsified more easily. In contrast to suspensions of the solid active compound, in emulsions the active compound is dissolved in the solvent droplets in molecular form and is thus more readily available and more effective on application. However, owing to the known problems caused by VOC, the use of relatively large amounts of organic solvents is, for reasons related to work hygiene, because of environmental aspects and in some cases also for toxicological reasons, not desirable.

A further disadvantage of conventional aqueous active compound preparations is the relatively large particle size of the active compound particles and active compound droplets suspended and emulsified, respectively, in the aqueous phase, whose size is generally in the region of several µm. However, what is desired are aqueous formulations in which the active compound is present in the most highly dispersed form possible, firstly to ensure uniform distribution in the formulation and thus better handling and dosing properties and to increase simultaneously the bioavailability of the active compound in the formulation. What is desired here are formulations in which the mean particle size in the phase comprising the active compound is below 500 nm and in particular below 300 nm.

There have been various proposals to use amphiphilic block copolymers for solubilizing water-insoluble active compounds in an aqueous vehicle. The term "solubilization" refers to a stable, uniform distribution of the water-insoluble active compound or effect substance achieved by using solubility-conveying substances (auxiliaries), where the particles of the disperse active compound phase are frequently so small that they hardly scatter visible light and the mixture therefore appears to be more or less transparent. Here, the amphiphilic block copolymers generally comprise at least one hydrophilic polymer block and at least one hydrophobic polymer block.

Thus, for example, US 2003/0009004 proposes for this purpose amphiphilic block copolymers comprising a hydrophilic polyethyleneimine block and a hydrophobic block of a biodegradable aliphatic polyester. However, this has the disadvantage that relatively large amounts of polymer, based on the active compound, are required to achieve stable aqueous active compound preparations.

US 2003/0157170 describes water-free active compound compositions comprising an amphiphilic diblock copolymer having a polyester as hydrophobic component and an additive. On dilution with water, the compositions form active compound-containing micelles. These compositions, too, have the disadvantage that relatively large amounts of polymer are required, based on the active compound.

WO 02/82900 describes the use of amphiphilic block copolymers for preparing aqueous suspensions of water-insoluble crop protection agents. The block copolymers used can be obtained by "living" or "controlled" free-radical block copolymerization of ethylenically unsaturated monomers. In addition to the fact that such processes are relatively complicated, the aqueous active compound formulations comprise relatively large amounts of water-soluble organic solvents. Moreover, the process requires the use of toxic transition metal catalysts which remain in the product. Moreover, the color of the block copolymers tends to change to brown.

U.S. Pat. No. 4,888,389 describes block copolymers having a polyisobutene block and a hydrophilic block, for example a polyether block. However, the applicant's own investigations have shown that the block copolymers described in this application are not suitable for preparing finely divided active compound preparations.

To summarize, it may be stated that, in spite of the general advantages offered for the formulation of water-insoluble active compounds and effect substances in water or aqueous media by amphiphilic block copolymers, the block copolymers known from the prior art are not entirely satisfactory, whether because their preparation is very complicated, the stability of the aqueous active compound preparations is unsatisfactory, the activity of the active compounds is adversely affected or large amounts of polymer, based on the active compound, are required, which, in addition to higher costs, may also be disadvantageous when using such preparations.

Accordingly, it is an object of the present invention to provide substances which enable effective solubilization of water-insoluble active compounds in an aqueous medium. In particular, these substances should be suitable for providing aqueous active compound compositions of water-insoluble active compounds, which compositions have a very low content, if any, of volatile organic compounds. Furthermore, it is desirable that the aqueous active compound compositions prepared using these substances have high stability with respect to breakdown on prolonged storage, when electrolytes are added and during dilution with water.

Surprisingly, this object is achieved by a polymer composition obtainable by reacting a) at least one hydrophobic polymer P1 which carries functional groups $R^{P1}$ which are reactive toward isocyanate groups and which is constructed of ethylenically unsaturated monomers M1, comprising:

a1) at least 10% by weight, based on the total amount of monomers M1, of monomers M1a of the formula I

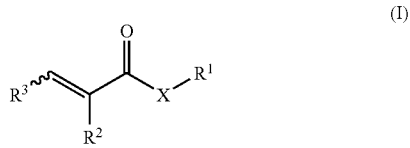

in which X is oxygen or a group $N-R^4$;
  $R^1$ is $C_1$-$C_{10}$-alkyl, $C_5$-$C_{10}$-cycloalkyl, phenyl or phenyl-$C_1$-$C_4$-alkyl;
  $R^2$ is hydrogen or $C_1$-$C_4$-alkyl;
  $R^3$ is hydrogen or $C_1$-$C_4$-alkyl; and
  $R_4$ is hydrogen or $C_1$-$C_4$-alkyl;

a2) up to 90% by weight, based on the total amount of monomers M1, of neutral monoethylenically unsaturated monomers M1b whose solubility in water at 25° C. is less than 50 g/l and which are different from the monomers M1a; and a3) up to 30% by weight, based on the total amount of monomers M1, of ethylenically unsaturated monomers M1c which are different from the monomers M1a and M1b, b) at least one hydrophilic polymer P2 which carries functional groups $R^{P2}$ which are reactive toward isocyanate groups, c) with at least one compound V which contains isocyanate groups and, with respect to the isocyanate groups, has a functionality of at least 1.5.

Accordingly, the present invention relates to the amphiphilic polymer compositions described herein and to the process for their preparation.

In an advantageous manner, the amphiphilic polymer compositions according to the invention are suitable for stabilizing poorly water-soluble or water-insoluble active compounds and effect substances in aqueous phase, thereby making it possible to prepare aqueous formulations of such active compounds and effect substances. In contrast to the block copolymers described in the prior art, they can be used to solubilize large amounts of active compound, based on the polymer, in the aqueous phase.

Accordingly, the present invention also provides the use of the amphiphilic polymer compositions described here and below for stabilizing poorly water-soluble or water-insoluble active compounds and/or effect substances in an aqueous medium.

Accordingly, the present invention also provides the use of the amphiphilic polymer compositions described herein for preparing formulations of water-insoluble or poorly water-soluble active compounds and effect substances which hereinafter are also referred to as active compound composition or effect substance composition. In this context, poor solubility is a solubility of the active compound or effect substance in water of less than 10 g/l, frequently less than 5 g/l, in particular less than 1 g/l and especially less than 0.1 g/l, at 25° C. and 1013 mbar.

The invention furthermore provides active compound compositions or effect substance compositions comprising at least one poorly water-soluble or water-insoluble active compound and/or effect substance and at least one amphiphilic polymer composition, as described here and below.

The active compound compositions or effect substance compositions according to the invention can be solid or liquid. A preferred embodiment of such a composition relates to an aqueous, i.e. liquid, active compound composition comprising an aqueous medium as continuous phase and at least one disperse phase comprising at least one active compound and/or effect substance having a solubility in water at 25° C./1013 mbar of less than 10 g/l, and at least one amphiphilic polymer composition.

The aqueous active compound compositions, prepared using amphiphilic block copolymers according to the invention, of poorly water-soluble or water-insoluble active compounds and/or effect substances comprise, in addition to an aqueous medium as continuous phase, at least one phase comprising active compound or effect substance, in which the active compound or the effect substance and the amphiphilic polymer composition are present in the form of aggregates of active compound or effect substance and the polymer components of the amphiphilic polymer composition. Thus, this phase comprising active compound or effect substance forms a disperse phase which comprises the active compound or the effect substance and at least one amphiphilic polymer composition according to the invention. In these compositions, the disperse phase is extremely finely divided, i.e. the particles of the disperse phase have particle sizes which are considerably less than 1 μm. In general, the mean particle diameter, which can be determined by light scattering, is not more than 500 nm, frequently not more than 300 nm and frequently in the range from 10 to 300 nm, preferably in the range from 10 to 250 nm, in particular in the range from 20 to 200 nm or 20 to 150 nm and particularly preferably in the range from 30 to 100 nm. In principle, the phase particles may have even smaller mean diameters up to a virtually molecularly disperse distribution with particle sizes below the limit detectable by light scattering (for example >10 nm).

A further preferred embodiment of the invention relates to a non-aqueous, generally solid or semi-solid, active compound composition comprising at least one active compound and/or effect substance which, having a solubility in water at 25° C./1013 mbar of less than 10 g/l, and at least one amphiphilic polymer composition, which comprises essentially no, or only small amounts, i.e. <10% by weight, of water. As further components, these compositions may comprise the auxiliaries and additives typical for the particular intended use.

On dilution, the compositions according to the invention, i.e. both aqueous and non-aqueous compositions, afford aqueous preparations of the active compound or effect substance, which preparations comprise an aqueous continuous phase and at least one phase comprising active compound or effect substance with mean particle sizes of considerably less than 1 μm, typically not more than 500 nm, frequently not more than 300 nm, for example in the range from 10 to 300 nm, preferably in the range from 10 to 250 nm, in particular in the range from 20 to 200 nm or 20 to 150 nm and particularly preferably in the range from 30 to 100 nm.

The stated particle sizes are weight-average particle sizes which can be determined by dynamic light scattering. The person skilled in the art is familiar with methods to achieve this, for example from H. Wiese in D. Distler, Wässrige Polymerdispersionen [Aqueous Polymer Dispersions], Wiley-VCH 1999, chapter 4.2.1, p. 40ff. and the literature cited therein, and also H. Auweter, D. Horn, J. Colloid Interf. Sci. 105 (1985) 399, D. Lilge, D. Horn, Colloid Polym. Sci. 269 (1991) 704 or H. Wiese, D. Horn, J. Chem. Phys. 94 (1991) 6429.

Here and below, the terms "aqueous medium" and "aqueous phase" include water, aqueous mixtures of water with up to 10% by weight, based on the mixture, of water-miscible organic solvents, and solutions of solids in water or in the aqueous mixtures. Examples of water-miscible solvents comprise $C_3$-$C_4$ ketones, such as acetone and methyl ethyl ketone, cyclic ethers, such as dioxane and tetrahydrofuran, $C_1$-$C_4$-alkanols, such as methanol, ethanol, n-propanol, isopropanol, n-butanol, tert-butanol, polyols and their mono- and dimethyl ethers, such as glycol, propanediol, ethylene glycol monomethyl ether, diethylene glycol, diethylene glycol monomethyl ether, diethylene glycol dimethyl ether, glycerol, furthermore $C_2$-$C_3$-nitriles, such as acetonitrile and propionitrile, dimethyl sulfoxide, dimethylformamide, formamide, acetamide, dimethylacetamide, butyrolactone, 2-pyrrolidone and N-methylpyrrolidone.

Here and below, the term "functionality" denotes the mean number of the respective functional groups per molecule or per polymer chain.

The aqueous active compound compositions according to the invention have extremely high stability to breakdown. Without breakdown occurring, they can be stored over a relatively long period of time of several months, even at elevated temperature and/or at highly variable temperatures. Additionally, without any problems, more concentrated dispersions can also be diluted with water without any breakdown phenomena, such as coagulation, crystallization, flocculation or sedimentation, taking place. Moreover, the compositions are highly tolerant to electrolytes. Additionally, owing to the extremely fine distribution, as a result of the very small particle diameter of the disperse phase, the activity of the active compounds is increased compared to conventional aqueous formulations. A further advantage of the aqueous active compound compositions according to the invention is that they can also be formulated as low-solvent compositions (content of volatile solvents <10% by weight, based on the weight of the active compound composition) or even as solvent-free compositions (content of volatile solvents <1% by weight, based on the weight of the active compound composition).

Both the hydrophobic polymers P1 used for preparing the amphiphilic polymer composition according to the invention and the hydrophilic polymers P2 have functional groups $R^{P1}$ and $R^{P2}$ respectively which are reactive toward isocyanate groups and react with the isocyanate group of the compound V, forming bonds. Examples of suitable functional groups are hydroxyl groups, mercapto groups (SH) and primary and secondary amino groups. Preferred functional groups are hydroxyl groups, in particular hydroxyl groups attached to an aliphatic or cycloaliphatic carbon atom.

Since the isocyanate group-containing compound V has, on average, at least 1.5 isocyanate groups per molecule, in the reaction of V with the polymer P1 and the polymer P2 at least some block copolymers are formed comprising both at least one hydrophobic polymer block derived from the hydrophobic polymer P1 and at least one hydrophilic polymer block derived from the hydrophilic polymer P2. In contrast to the amphiphilic block copolymers of the prior art, the blocks are attached to one another not directly but via a linker which has at least two urethane and/or urea groups. In contrast to the block copolymers of the prior art, the amphiphilic polymer compositions obtained generally also comprise minor amounts of unreacted polymers P1 and/or P2 and also symmetrical reaction products having polymer blocks derived either exclusively from polymers P1 or polymer blocks derived exclusively from polymers P2. However, the advantageous amphiphilic properties of the polymer composition are ensured.

Suitable hydrophobic polymers P1 are, in principle, all polymers constructed of ethylenically unsaturated monomers M1, which polymers comprise, based on the total amount of monomers M1, at least 10% by weight, preferably at least 30% by weight, in particular at least 50% by weight, particularly preferably at least 60% by weight of monomers M1a and have the required number of reactive groups $R^{P1}$.

Preferred monomers M1a are those in which $R^3$ in formula I is hydrogen. $R^2$ is preferably hydrogen or methyl. X is preferably O, NH, $NCH_3$ or $NC_2H_5$.

$R^1$ is preferably
  $C_1$-$C_{10}$-alkyl, such as methyl, ethyl, n-propyl, isopropyl, n-butyl, 2-butyl, isobutyl, tert-butyl, 1-pentyl, 2-pentyl, neopentyl, n-hexyl, 2-hexyl, n-octyl, 2-ethylhexyl, 2-propylheptyl or n-decyl, where for $R^2$=H, $R^1$ is in particular different from methyl;
  $C_5$-$C_{10}$-cycloalkyl, such as cyclopentyl, cyclohexyl or methylcyclohexyl, or
  phenyl-$C_1$-$C_4$-alkyl, such as benzyl, 1- or 2-phenylethyl, 1-, 2- or 3-phenylpropyl.
$R^1$ is in particular $C_1$-$C_{10}$-alkyl, where for $R^2$=H, $R^1$ is in particular different from methyl.

Accordingly, particularly preferred monomers M1a are the esters of acrylic acid with $C_2$-$C_{10}$-alkanols (=$C_2$-$C_{10}$-alkyl acrylates), such as ethyl acrylate, n-butyl acrylate, isobutyl acrylate, tert-butyl acrylate, n-hexyl acrylate, 2-ethylhexyl acrylate and 3-propylheptyl acrylate, the esters of methacrylic acid with $C_1$-$C_{10}$-alkanols, such as methyl methacrylate, ethyl methacrylate, n-butyl methacrylate, isobutyl methacrylate, tert-butyl methacrylate and n-hexyl methacrylate. Preferred monomers M1a are furthermore the N-($C_2$-$C_{10}$-alkyl)amides of acrylic acid and methacrylic acid, and also the N-($C_1$-$C_2$-alkyl)-N-($C_2$-$C_{10}$-alkyl)amides of acrylic acid and methacrylic acid, for example N-ethylacrylamide, N,N-diethylacrylamide, N-butylacrylamide, N-methyl-N-propylacrylamide, N-(n-hexyl)acrylamide, N-(n-octyl)acrylamide and the corresponding methacrylamides. Based on the total amount of monomers M1a, the monomers M1a in particular comprise at least 50% by weight, in particular at least 70% by weight, of at least one $C_1$-$C_4$-alkyl methacrylate ($R^1$=$C_1$-$C_4$-alkyl, $R^2$=$CH_3$ and $R^3$=H), and from among these particularly preferably methyl methacrylate.

In addition to the monomers M1a, the hydrophobic polymer P1 may also comprise monomers M1b different from the monomers M1a, in an amount of up to 90% by weight, preferably up to 70% by weight, in particular up to 50% by weight and particularly preferably up to 40% by weight, based on the total amount of monomers M1. These are monoethylenically unsaturated monomers having a solubility in water of <50 g/l and frequently <20 g/l, at 25° C. and 1013 mbar. Examples of such monomers M1b are vinylaromatic monomers, such as styrene, α-methylstryene, vinyltoluene, etc., olefins having 2 to 10 carbon atoms, preferably α-olefins having 3 to 10 carbon atoms, such as propene, 1-butene, 1-pentene, 1-hexene, 1-octene and 1-decene, vinyl esters of aliphatic carboxylic acids, such as vinyl acetate, vinyl propionate, vinyl laurate, vinyl nonanoate, vinyl decanoate, vinyl laurate and vinyl stearate, unsaturated nitriles, such as acrylonitrile and methacrylonitrile, halogenated olefins, such as vinyl chloride, $C_{11}$-$C_{20}$-alkyl esters of monoethylenically unsaturated monocarboxylic acids having preferably 3 to 6 carbon atoms, for example $C_{11}$-$C_{20}$-alkyl acrylates and $C_{11}$-$C_{20}$-alkyl methacrylates, such as lauryl acrylate, lauryl methacrylate, isotridecyl acrylate, isotridecyl methacrylate, stearyl acrylate, stearyl methacrylate, di-$C_1$-$C_{20}$-alkyl esters of ethylenically unsaturated dicarboxylic acids having preferably 4 to 8 carbon atoms, for example di-$C_1$-$C_{20}$-alkyl esters of fumaric acid and maleic acid, such as dimethyl fumarate, dimethyl maleate, dibutyl fumarate and dibutyl maleate, glycidyl esters of monoethylenically unsaturated monocarboxylic acids having preferably 3 to 6 carbon atoms, such as glycidyl acrylate and glycidyl methacrylate. Preferred monomers M1b are vinylaromatic monomers and from among these in particular styrene. In one embodiment, the proportion of the monomers M1b is from 1 to 90% by weight, preferably from 5 to 70% by weight, in particular from 7 to 50% by weight and particularly preferably from 10 to 40% by weight, based on the total amount of monomers M1. Preferably, the total amount of monomers M1a and M1b is at least 80% by weight, in particular at least 90% by weight and particularly preferably at least 95% by weight of the monomers M1.

In addition to the monomers M1a and, if appropriate, M1b, the polymers P1 may comprise up to 30% by weight, frequently not more than 20% by weight, in particular not more than 10% by weight or not more than 5% by weight, based on the total amount of monomers M1, of ethylenically unsaturated monomers M1c different from the monomers M1a and M1b.

The monomers M1c are preferably selected from neutral monoethylenically unsaturated monomers M1c.1 whose solubility in water at 25° C. is at least 50 g/l and in particular at least 100 g/l and monoethylenically unsaturated monomers M1c.2 which carry at least one ionic or ionizable group.

Examples of monomers M1c.1 are the amides of the above-mentioned ethylenically unsaturated carboxylic acids, in particular acrylamide and methacrylamide, and also N-hydroxyalkylamides, in particular N-hydroxymethylamides, of the above-mentioned ethylenically unsaturated carboxylic acids, in particular N-methylolacrylamide and N-methylolmethacrylamide, ethylenically unsaturated nitriles, such as methacrylonitrile and acrylonitrile, hydroxyalkyl esters of the abovementioned α,β-ethylenically unsaturated $C_3$-$C_8$-monocarboxylic acids and of the $C_4$-$C_8$-dicarboxylic acids, in particular hydroxyethyl acrylate, hydroxyethyl methacrylate, 2- and 3-hydroxypropyl acrylate, 2- and 3-hydroxypropyl methacrylate, vinyl ethers and allyl ethers of polyethylene glycols or of alkylpolyethylene glycols, esters of the above-mentioned monoethylenically unsaturated mono- and dicarboxylic acids with $C_2$-$C_4$-polyalkylene glycols, in particular the esters of these carboxylic acids, especially of acrylic acid or methacrylic acid, with polyethylene glycol or alkylpolyethylene glycols, where the (alkyl)polyethylene glycol radical in such esters and ethers usually has a molecular weight in the range from 100 to 3000. The monomers M1c.1 furthermore include N-vinyl amides, such as N-vinylformamide, N-vinylpyrrolidone and N-vinylcaprolactam. The monomers M1c.1 furthermore include urea group-carrying monomers, such as N-(2-acrylamidoethyl)imidazolin-2-one and N-(2-methacrylamidoethyl)imidazolin-2-one, and monomers which contain aldehyde or keto groups, such as 3-(acrylamido)-3-methylbutan-2-one (diacetoneacrylamide), 3-(methacrylamido)-3-methylbutan-2-one, 2,4-dioxapentyl acrylate and 2,4-dioxapentyl methacrylate. The proportion of monomers M1c.1 is preferably not more than 20% by weight and in particular not more than 10% by weight, for example from 0.1 to 10 and in particular from 0.5 to 5% by weight, based on the total amount of monomers M1.

The monomers M1c.2 include, in particular, monoethylenically unsaturated monomers M1c.2s which contain at least one acid group or at least one anionic group, in particular monomers which contain a sulfonic acid group, a phosphonic acid group or one or two carboxylic acid groups, and also the salts of such monomers, in particular the alkali metal salts, for example the sodium or potassium salts and also the ammonium salts. These include ethylenically unsaturated sulfonic acids, in particular vinylsulfonic acid, 2-acrylamido-2-methylpropanesulfonic acid, 2-acryloxyethanesulfonic acid and 2-methacryloxyethanesulfonic acid, 3-acryloxy- and 3-methacryloxypropanesulfonic acid, vinylbenzenesulfonic acid and their salts, ethylenically unsaturated phosphonic acids, such as vinylphosphonic acid and vinylphosphonic acid dimethyl ester and their salts, and α,β-ethylenically unsaturated $C_3$-$C_8$-mono- and $C_4$-$C_8$-dicarboxylic acids, in particular acrylic acid, methacrylic acid, crotonic acid, maleic acid, fumaric acid and itaconic acid. The proportion of monomers M1c.2s will frequently not be more than 20% by weight, for example from 0.1 to 20% by weight and in particular from 0.5 to 15% by weight, based on the total amount of monomers M1. In a preferred embodiment, the polymer P1 comprises no or less than 0.1% by weight of monomers M1c.2s.

The monomers M1c.2 furthermore include monoethylenically unsaturated monomers M1c.2k which have at least one cationic group and/or at least one group which can be protonated in aqueous medium. The monomers M1c.2k include in particular those which have a protonatable amino group, a quaternary ammonium group, a protonatable imino group or a quaternized imino group. Examples of monomers having a protonatable imino group are N-vinylimidazole and vinylpyridines. Examples of monomers having a quaternized imino group are N-alkylvinylpyridinium salts and N-alkyl-N'-vinylimidazolinium salts, such as N-methyl-N'-vinylimidazolinium chloride or methosulfate. From among the monomers M1c.2k, particular preference is given to the monomers of the formula II

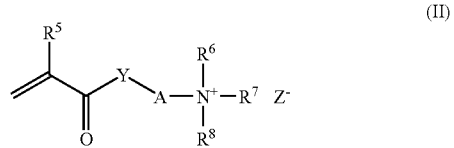

in which
$R^5$ is hydrogen or $C_1$-$C_4$-alkyl, in particular hydrogen or methyl,
$R^6$, $R^7$ independently of one another are $C_1$-$C_4$-alkyl, in particular methyl and
$R^8$ is hydrogen or $C_1$-$C_4$-alkyl, in particular hydrogen or methyl,
Y is oxygen, NH or $NR^9$, where $R^9$=$C_1$-$C_4$-alkyl,
A is $C_2$-$C_8$-alkylene, for example 1,2-ethanediyl, 1,2- or 1,3-propanediyl, 1,4-butanediyl or 2-methyl-1,2-propanediyl, which may be interrupted by 1, 2 or 3 nonadjacent oxygen atoms, and
$Z^-$ is an anion equivalent, for example $Cl^-$, $HSO_4^-$, $½SO_4^{2-}$ or $CH_3OSO_3^-$, etc., and, for $R^8$=H, the free bases of the monomers of the formula II.

Examples of such monomers M1c.2k are 2-(N,N-dimethylamino)ethyl acrylate, 2-(N,N-dimethylamino)ethyl methacrylate, 2-(N,N-dimethylamino)ethylacrylamide, 3-(N,N-dimethylamino)propylacrylamide, 3-(N,N-dimethylamino)propylmethacrylamide, 2-(N,N-dimethylamino)ethylmethacrylamide, 2-(N,N,N-trimethylammonium)ethyl acrylate chloride, 2-(N,N,N-trimethylammonium)ethyl methacrylate chloride, 2-(N,N,N-trimethylammonium)ethylmethacrylamide chloride, 3-(N,N,N-trimethylammonium) propylacrylamide chloride, 3-(N,N,N-trimethylammonium) propylmethacrylamide chloride, 2-(N,N,N-trimethylammonium)ethylacrylamide chloride, and the corresponding metosulfates and sulfates. Further suitable monomers M1c.2k are vinylpyridines and vinylimidazole and their quaternization products.

The proportion of monomers M1c.2k is advantageously not more than 20% by weight, for example from 0.1 to 20% by weight, in particular from 0.5 to 15% by weight and especially from 1 to 10% by weight, based on the total amount of monomers M1. In a preferred embodiment, the polymer P1 comprises no or not more than 0.1% by weight of monomers M1c.2k.

The monomers M1c also include monomers M1c.3 having two or more nonconjugated ethylenically unsaturated double bonds. The proportion of such monomers M1c.3 is generally not more than 2% by weight and in particular not more than 0.5% by weight, based on the total amount of monomer M1. Examples of these are vinyl and allyl esters of monoethylenically unsaturated carboxylic acids, such as allyl acrylate and allyl methacrylate, di- and polyacrylates of di- or polyols, such as ethylene glycol diacrylate, ethylene glycol dimethacrylate, butanediol diacrylate, butanediol dimethacrylate, hexanediol diacrylate, hexanediol dimethacrylate, triethylene glycol diacrylate, triethylene glycol trimethacrylate, tris(hydroxymethyl)ethane triacrylate and tris(hydroxymethyl)ethane trimethacrylate, pentaerythritol triacrylate and pentaerythritol trimethacrylate, furthermore the allyl and methallyl esters of polyfunctional carboxylic acids, such as diallyl maleate, diallyl fumarate, diallyl phthalate. Typical monomers M1c.3 are also compounds such as divinylbenzene, divinylurea, diallylurea, triallyl cyanurate, N,N'-divinyl- and N,N'-diallylimidazolidin-2-one, and also methylenebisacrylamide and methylenebismethacrylamide.

According to the invention, the polymers P1 carry reactive functional groups $R^{P1}$ which react with the isocyanate groups forming bonds. The mean number of such groups per polymer molecule (functionality) is generally not more than two and preferably in the range from 0.3 to 1.8, in particular in the range from 0.5 to 1.5 and especially in the range from 0.6 to 1.4. The functional group $R^{P1}$ may be located in the polymer chain and is preferably at the end of the polymer chain.

With a view to the use of the amphiphilic polymer composition according to the invention for formulating active compounds, the hydrophobic polymer P1 preferably has a number-average molecular weight in the range from 500 to 20 000 dalton and in particular in the range from 1500 to 15 000 dalton.

In principle, polymers P1 are known from the prior art, for example from U.S. Pat. No. 5,556,918 and EP-A 742 238. They are generally prepared by free-radical-initiated solvent polymerization of the monomers M1 in the presence of an initiator and, if appropriate, a regulator, with the proviso that the initiator, on decomposition, contains a hydroxyl radical (.OH radical) and/or the regulator contains an OH group or an $NH_2$ group. Suitable initiators are organic hydroperoxides, such as tert-butyl hydroperoxide, tetrahydrofuran hydroperoxide, cumene hydroperoxide or 2,2'-azobis(2-methyl-N-(2-hydroxyethyl)propionamide). Suitable regulators are aminoalcohols, aminophenols and in particular thioalkanols, such as 3-hydroxypropanethiol, 2-hydroxyethyl-3-mercaptopropionic esters and especially 2-hydroxyethanethiol (mercaptoethanol). If such as regulator is used, the polymerization can also be carried out in the presence of a conventional initiator, for example a conventional azo initiator or an organic peroxide, such as azobis(isobutyronitrile), di-(tert-butyl) peroxide, didecanoyl peroxide, dibenzoyl peroxide, tert-butyl peracetate or tert-butyl 2-methylperpropionate. If the polymerization is carried out in the presence of one of the regulators mentioned above, the regulator will generally be employed in an amount of from 0.1 to 5% by weight, frequently from 0.2 to 4% by weight and in particular from 0.5 to 3% by weight, based on the total amount of monomers M1. Initiators are generally employed in an amount of from 0.05 to 5% by weight, frequently from 0.1 to 4% by weight and particularly preferably in an amount of from 0.2 to 3% by weight, based on the monomers M1 to be polymerized. For further details, reference is made in particular to page 3 of EP 742 238 whose disclosure is expressly incorporated herein by way of reference.

The person skilled in the art is, in principle, familiar with hydrophilic polymers P2 having reactive groups $R^{P2}$. These are generally polymers which per se are soluble in water. The solubility of the polymers in water may be mediated by neutral hydrophilic groups, such as carboxamide groups, ether groups, lactam groups, oxazolidine groups, by anionic groups or by acidic groups, for example carboxylate groups, sulfonate groups or phosphate groups, by basic groups, for example by primary or secondary amino groups, imidazole groups, pyridine groups, or by cationic groups, for example quaternized ammonium groups, quaternized pyridine groups or quaternized imidazole groups. Accordingly, depending on the nature of the groups, there is a distinction between nonionic hydrophilic polymers P2, anionic or acidic polymers P2 and basic or cationic polymers P2. The polymer P2 is preferably a nonionic polymer, i.e. the proportion of ionic groups or acidic or basic groups is not more than 0.5 mol/kg of polymer P2 and in particular not more than 0.1 mol/kg of polymer P2.

Examples of nonionic polymers P2 are:

aliphatic polyethers which are constructed to at least 50% by weight and in particular to at least 70% by weight from ethylene oxide units, homo- and copolymers of ethylenically unsaturated monomers comprising at least 50% by weight, in particular at least 70% by weight, based on the total amount of monomers M2, of at least one monoethylenically unsaturated hydrophilic monomer M2a having a solubility in water of >50 g/l and in particular >100 g/l, at 25° C./1013 mbar. Suitable monomers M2a are the monomers mentioned as monomers M1c.1, in particular N-vinyllactams, such as N-vinylpyrrolidone and N-vinylcaprolactam, the abovementioned amides of monoethylenically unsaturated monocarboxylic acids, such as methacrylamide, acrylamide, the abovementioned hydroxyalkyl esters of monoethylenically unsaturated monocarboxylic acids, such as hydroxyethyl acrylate and hydroxyethyl methacrylate, vinyl esters and allyl esters of polyethylene glycol and of alkylpolyethylene glycols, and also the esters of acrylic acid and methacrylic acid with polyethylene glycols or alkylpolyethylene glycols, poly(2-methyloxazolines) and poly(2-ethyloxazolines), and poly(α-hydroxycarboxylic acid) esters, such as polyglycolide and polylactide.

Examples of suitable anionic polymers P2 are those comprising at least 30% by weight and preferably at least 50% by weight, based on the total weight of the polymer P2, of monoethylenically unsaturated monomers M2b carrying an acid group, for example a carboxyl group, a sulfonic acid group, a phosphate group or a phosphonic acid group. Examples of suitable monomers M2b are the monomers M1c.2s mentioned in connection with polymers P1, for example α,β-ethylenically unsaturated mono- and dicarboxylic acids, such as acrylic acid, methacrylic acid, vinylacetic acid, monoethylenically unsaturated sulfonic acids, such as vinyl sulfonate, methallyl sulfonate, styrenesulfonic acid, 2-acrylamido-2-methylpropanesulfonic acid and 2-acryloxyethylsulfonic acid, ethylenically unsaturated phosphonic acids, such as vinyl phosphonate, allyl phosphonate, methallyl phosphonate, 2-acrylamido-2-methylpropanephosphonic acid and 2-acryloxyethyl phosphonate. In addition to the monomers M2b mentioned above, suitable anionic polymers P2 may comprise up to 50% by weight and in particular up to 30% by weight of monomers M1a and M1b and also up to 70% by weight of monomers M2a.

Examples of suitable cationic polymers P2 are homo- and copolymers of the abovementioned monoethylenically unsaturated monomers M1c.2k, and also copolymers of the monomers M1c.2k with the monoethylenically unsaturated neutral monomers M1c.1.

From among the polymers P2, particularly preference is given to those which, with respect to the functional groups $R^{P2}$, have a functionality F2 in the range from 0.5 to 3 and in particular in the range from 0.6 to 2.5.

The number-average molecular weight of the polymers P2, determined by GPC according to customary methods, is preferably in the range from 500 to 20 000 dalton and in particular in the range from 800 to 15 000 dalton.

From among the polymers P2, preference is given in particular to aliphatic polyethers which are constructed to at least 50% by weight and in particular at least 70% by weight and particularly preferably at least 90% by weight, based on their total weight, of ethylene oxide units. In addition, the aliphatic polyethers may have structural units derived from $C_3$-$C_4$-alkylene oxides. The polyethers may also have an end group different from hydrogen. Particularly preferred polyethers are in particular those of the formula II

$$R^a\text{—}X\text{—}(CHR^b\text{—}CH_2\text{—}O)_p\text{—}H \quad (III)$$

in which
$R^a$ is hydrogen, $C_1$-$C_{20}$-alkyl or benzyl,
X is oxygen or NH,
$R^b$ is hydrogen or methyl, where at least 50 mol %, in particular at least 70 mol % and preferably at least 90 mol % of the groups $R^2$ are hydrogen,
p is an integer whose mean is in the range from 10 to 500, preferably from 20 to 250 and in particular from 25 to 100 (number-average).

The person skilled in the art is familiar with suitable hydrophilic polymers P2 and most of them are commercially available, for example under the trade names Pluriol® and Pluronic® (polyethers from BASF Aktiengesellschaft), Sokalan®, Kollidon® (homo- and copolymers of the monomers M2a, M2b and M1c.2k), or they can be prepared by standard methods.

The total proportion of hydrophobic polymers P1 in the amphiphilic polymer composition, i.e. the total amount of reacted and unreacted polymer P1, is preferably from 9 to 90 and in particular from 20 to 68% by weight of the total weight of polymer P1, polymer P2 and compound V.

The total proportion of hydrophobic polymers P2 in the amphiphilic polymer composition, i.e. the total amount of reacted and unreacted polymer P2, is preferably from 9 to 90 and in particular from 30 to 78% by weight of the total weight of polymer P1, polymer P2 and compound V.

The total proportion of compound V in the amphiphilic polymer composition, i.e. the total amount of compound V employed, is preferably from 1 to 20 and in particular from 2 to 15% by weight of the total weight of polymer P1, polymer P2 and compound V.

The weight ratio of polymers P1 and P2 in the amphiphilic polymer composition, in each case calculated as the total amount of polymers used for the preparation, is preferably in the range from 1:10 to 10:1 and in particular in the range from 1:4 to 2.2:1.

Suitable compounds V having, with respect to the isocyanate groups, a functionality of at least 1.5, in particular from 1.5 to 4.5 and especially from 1.8 to 3.5, comprise aliphatic, cycloaliphatic and aromatic di- and polyisocyanates and also the isocyanurates, allophanates, uretdiones and biurets of aliphatic, cycloaliphatic and aromatic diisocyanates.

The compounds V preferably have, on average, 1.8 to 3.5 isocyanate groups per molecule. Examples of suitable compounds V are aromatic diisocyanates, such as toluene 2,4-diisocyanate, toluene 2,6-diisocyanates, commercially available mixtures of toluene 2,4- and 2,6-diisocyanate (TDI), n-phenylene diisocyanate, 3,3'-diphenyl-4,4'-biphenylene diisocyanate, 4,4'-biphenylene diisocyanate, 4,4'-diphenylmethane diisocyanate, 3,3'-dichloro-4,4'-biphenylene diisocyanate, cumene 2,4-diisocyanate, 1,5-naphthalene diisocyanate, p-xylylene diisocyanate, p-phenylene diisocyanate, 4-methoxy-1,3-phenylene diisocyanate, 4-chloro-1,3-phenylene diisocyanate, 4-ethoxy-1,3-phenylene diisocyanate, 2,4-dimethylene-1,3-phenylene diisocyanate, 5,6-dimethyl-1,3-phenylene diisocyanate, 2,4-diisocyanatodiphenyl ether, aliphatic diisocyanates, such as ethylene diisocyanate, ethylidene diisocyanate, propylene 1,2-diisocyanate, 1,6-hexamethylene diisocyanate, 1,4-tetramethylene diisocyanate, 1,10-decamethylene diisocyanate, and cycloaliphatic diisocyanates, such as isophorone diisocyanate (IPDI), cyclohexylene 1,2-diisocyanate, cyclohexylene 1,4-diisocyanate and bis(4,4'-isocyanatocyclohexyl)methane. From among the diisocyanates, preference is given to those whose isocyanate groups differ in their reactivity, such as toluene 2,4-diisocyanate, toluene 2,6-diisocyanate, mixtures thereof and cis- and trans-isophorone diisocyanate.

In another preferred embodiment of the invention, a biuret or an isocyanurate of an aliphatic or cycloaliphatic diisocyanate compound, for example the cyanurate of tetramethylene diisocyanate or of hexamethylene diisocyanate, is used to prepare the amphiphilic polymer composition according to the invention.

To prepare the amphiphilic polymer composition according to the invention, the hydrophobic polymer P1 and the hydrophilic polymer P2 are reacted successively or simultaneously with the compound V, under reaction conditions where the groups $R^{P1}$ and/or $R^{P2}$ react with the isocyanate groups with bond formation.

The reaction can be carried out in the absence or in the presence of small amounts of customary catalysts which promote the formation of urethanes or ureas. Suitable catalysts are, for example, tertiary amines, for example triethylamine, tri-n-propylamine, N-methylpyrrolidine, N-methylpiperidine and diazabicyclooctane (DABCO), organotin compounds, in particular dialkyltin(IV) salts of aliphatic carboxylic acids, such as dibutyltin dilaurate and dibutyltin dioctoate, tin(II) dialkanoates, such as tin dioctoate, and also cesium salts, such as cesium acetate. If desired, the catalyst is employed in an amount of not more than 0.1% by weight, based on the compound V, for example in an amount of from 0.01 to 0.1% by weight, in particular up to 0.05% by weight.

The required reaction temperatures depend, of course, on the reactivity of the functional group $R^{P1}$ or $R^{P2}$ and on the isocyanate compound V and, if employed, on the type and the amount of catalyst used. They are generally in the range from 10 to 120° C. and in particular in the range from 15 to 85° C.

It is self-evident that the reaction of the polymers P1 and P2 with the isocyanate compound V is carried out in the absence of moisture (water content preferably <10 000 ppm and in particular <2000 ppm).

The reaction can be carried out neat or in an organic solvent which is inert to the isocyanate groups of the compound V. Examples of suitable solvents are aliphatic ketones, such as acetone, methyl ethyl ketone, cyclohexanone, alkyl esters of aliphatic carboxylic acids, such as methyl acetate, ethyl acetate, methyl propionate, ethyl propionate, n-butyl acetate, alicyclic and cyclic ethers, such as diethyl ether, diisopropyl ether, methyl tert-butyl ether, tetrahydrofuran, aromatic, aliphatic and alicyclic hydrocarbons, such as toluene, xylenes, hexane, cyclohexane, and also N-alkyllactams, such as N-methylpyrrolidone, and mixtures of these solvents.

The reaction of the polymer P1 and the polymer P2 with the compound V can be carried out successively or simultaneously, i.e. polymers P1 and P2 can be reacted one after the other or both at the same time with the compound V.

If the polymers P1 and P2 are reacted with the compound V one after the other, it is possible both to react initially polymer P1 with the compound V and then polymer P2 with the compound V, and vice versa.

If the polymers P1 and P2 are reacted successively with the compound V, the reaction is preferably carried out such that, after the reaction with the first polymer P1 or P2 has ended, at least 10 mol % to 90 mol %, in particular 20 mol % to 80 mol %, of the isocyanate groups in V have reacted with the functional groups $R^1$ and/or $R^2$, and 10 to 90 mol %, in particular 20 to 80 mol %, of the isocyanate groups present are still available. This is followed by the reaction with the second polymer P1 or P2. Accordingly, the first polymer P1 or P2 is preferably employed in an amount such that the molar ratio of reactive groups $R^{P1}$ and/or $R^{P2}$ to the number of isocyanate groups per molecule V is in the range from 0.1:1 to 0.9:1 and in particular in the range from 0.2:1 to 0.8:1. The product obtained in this manner is then reacted with the second polymer, the second polymer P1 or P2 preferably being employed in an amount such that the total amount of reactive groups $R^{P1}+R^{P2}$ corresponds at least to the number of isocyanate groups of the compound V. Preferably, the ratio $R^{P1}+R^{P2}$ to the total amount of isocyanate groups will not exceed a value of 1.2:1.

If the polymers P1 and P2 are reacted simultaneously with the isocyanate compound V, the polymers P1 and P2 are preferably employed in an amount such that the molar ratio of reactive groups $R^{P1}+R^{P2}$ to the isocyanate groups is at least 1:1. Preferably, the ratio $R^{P1}+R^{P2}$ to the total amount of isocyanate groups will not exceed a value of 1.2:1.

In the reaction, the isocyanate compound V can be employed as such. However, it is also possible to employ the isocyanate compound V in a form where some of the isocyanate groups are reversibly blocked by a protective group. Many compounds which block (cap or protect) isocyanate groups have been described in the literature (cf., for example, Z. W. Wicks, Prog. Org. Coat. 3 (1975) 73-99 and 9 (1981) 3-28 or Houben-Weyl, Methoden der Organischen Chemie [Methods of Organic Chemistry], Vol. XIV/2, p. 61 ff., Georg Thieme Verlag, Stuttgart 1963). Examples of isocyanate group-blocking agents which may be mentioned are phenols, caprolactam, imidazoles, pyrazoles, pyrazolinones, 1,2,4-triazoles, diketopiperazines, malonic esters and oximes. However, to achieve the results according to the invention, it is not necessary to employ isocyanates which are partially blocked in a reversible manner.

In a particularly preferred embodiment of the invention, in a first reaction step, the hydrophobic polymer P1 is prepared in the manner described above by free-radical solvent polymerization, and the reaction with the isocyanate V is carried out in the resulting liquid reaction mixture in the manner described herein, without prior isolation of the polymer P1. The resulting reaction mixture is then reacted with polymer P2, preferably with a polyether. Alternatively, the desired amount of polymer P2 may be added to the polymer P1 prepared in this manner, followed by reaction with compound V.

To prepare the aqueous active compound formulations, the polymer composition obtained according to the invention can be isolated from the reaction mixture. However, it is also possible to use the reaction mixture as such.

In a preferred embodiment of the invention, the solvent employed for preparing the polymer composition is partially or completely replaced by water, which gives an aqueous dispersion of the amphiphilic polymer composition. This can be achieved, for example, by initially removing the solvent by distillation and then dispersing the residue in water or an aqueous medium. It is also possible to add water to the solution of the polymer composition and to remove the solvent after the addition of the water, or at the same time.

The active compound or effect substance composition according to the invention can be prepared by different routes. Typically, the preparation of the active compound or effect substance composition according to the invention comprises the preparation or provision of a homogeneous non-aqueous mixture comprising the amphiphilic polymer composition and at least one active compound and/or effect substance.

In a first embodiment of the present invention, the aqueous active compound composition is prepared by initially preparing a homogeneous non-aqueous mixture comprising amphiphilic polymer composition and active compound and/or effect substance and then dispersing the resulting mixture in water or an aqueous medium.

To prepare the homogeneous non-aqueous mixture, the active compound is generally incorporated into a liquid form of the amphiphilic polymer composition, for example a melt or, preferably, a solution in an organic solvent. If a solvent is used, the solvent is subsequently substantially and preferably completely removed, giving a solid solution of the active compound in the amphiphilic polymer composition. Solvents suitable for this purpose are, in principle, those capable of dissolving both the active compound and the polymer, for example aliphatic nitriles, such as acetonitrile and propionitrile, N,N-dialkylamides of aliphatic carboxylic acids, such as dimethylformamide and dimethylacetamide, N-alkyllactams. such as N-methylpyrrolidone, the aliphatic and alicyclic ethers mentioned above, for example tetrahydrofuran, halogenated hydrocarbons, such as dichloromethane, dichloroethane, and mixtures of the solvents mentioned above. To prepare the aqueous composition according to the invention, the resulting solid solution of the active compound in the amphiphilic polymer composition is then dispersed by stirring in an aqueous medium. Stirring can be carried out at temperatures in the range of ambient temperature or else at elevated temperature, for example at a temperature in the range from 10 to 80° C. and in particular in the range from 20 to 50° C.

In a second embodiment of the present invention, the preparation of the aqueous active compound composition is prepared by incorporating the active compound and/or effect substance into an aqueous solution/dispersion of the amphiphilic polymer composition. This is generally achieved by carrying out the incorporation at a temperature above the melting point of the active compound or effect substance and preferably at a temperature where the active compound or effect substance melt has a low viscosity, i.e. a viscosity in the range from 1 to 1000 mPa·s (according to DIN 53019-2 at 25° C.). The incorporation is preferably carried out using strong shear forces, for example in an Ultraturrax.

In a third embodiment of the invention, the aqueous active compound composition is prepared by a process which comprises the following steps a to c:
a) preparing a solution of active compound and/or effect substance and, if appropriate, amphiphilic polymer composition in an organic solvent having a boiling point below that of water and
b) mixing the solution of the active compound and/or effect substance with water or an aqueous solution of the amphiphilic copolymer and
c) removing the solvent.

Alternatively, this may be carried out in a manner where the solution of the active compound comprises the amphiphilic polymer composition, and this solution is mixed with water, or where the solution of the active compound comprises only part of the amphiphilic polymer composition or no amphiphilic polymer composition, and this solution is mixed with an aqueous solution or dispersion of the amphiphilic polymer composition. Mixing may be carried out in suitable stirring vessels, it being possible either to initially charge water or the aqueous solution of the amphiphilic polymer composition and to add the solution of the active compound or effect substance, or, alternatively, to initially charge the solution of the active compound or effect substance and to add the water or the aqueous solution of the amphiphilic polymer composition. The organic solvent is then removed, for example by distillation, where, if appropriate, water is added.

In a preferred variant of this embodiment, the active compound solution and the water or the aqueous solution of the amphiphilic polymer composition are/is continuously added to a mixing zone, and the mixture, from which the solvent is then removed, is continuously removed from the mixing zone. The mixing zone can be designed as desired. In principle, all apparatus which allows continuous mixing of liquid streams is suitable for this purpose. Such apparatus is known, for example, from Continuous Mixing of Fluids (J.-H. Henzler) in Ullmann's Encyclopedia 5th ed. on CD-Rom, Wiley-VCH. The mixing zone may be designed as a static or dynamic mixer or mixed forms thereof. Suitable mixing zones are in particular also jet mixers or comparable mixers having nozzles. In a preferred embodiment, the mixing zone is the apparatus described in "Handbook of Industrial Crystallization" (A. S. Myerson, 1993 Butterworth-Heinemann, page 139, ISBN 0-7506-9155-7) or a comparable apparatus.

The volume ratio of active compound solution to water or aqueous solution of the amphiphilic polymer composition can be varied over a wide range and is preferably in the range 10:1 to 1:20 and in particular in the range from 5:1 to 1:10.

The nature of the solvent should be such that the amphiphilic polymer composition and the active compound are dissolved in the desired ratios. By standard experiments, the person skilled in the art is able to determine suitable solvents. Examples of suitable solvents are $C_2$-$C_4$-alkanols, such as ethanol, n-propanol, n-butanol, isobutanol, the aliphatic and alicyclic ethers mentioned above, such as diethyl ether, diisopropyl ether, methyl tert-butyl ether, dioxane, tetrahydrofuran, ketones such as acetone, methyl ethyl ketone.

In a further embodiment of the present invention, a non-aqueous active compound composition is prepared by preparing a homogeneous non-aqueous mixture of amphiphilic polymer composition and active compound and/or effect substance. Provided that this composition does not comprise any liquid components, it is generally solid. With respect to the preparation of such compositions, what was said above in the context of the first embodiment for preparing a homogeneous non-aqueous mixture comprising amphiphilic polymer composition and active compound and/or effect substance applies in an analogous manner; however, at this stage, it is possible to incorporate, if appropriate, desired additives and auxiliaries into the composition, in a manner known per se. This variant is particularly suitable for preparing non-aqueous compositions.

It has been found to be advantageous if the weight ratio of active compound and/or effect substance to the amphiphilic polymer composition in the aqueous active compound compositions according to the invention is in the range from 1:10 to 3:1 and in particular in the range from 1:5 to 2:1.

The content of active compound and/or effect substance can be varied over wide ranges. In particular, using the amphiphilic polymer compositions, it is possible to prepare active compound concentrates which comprise the active compound in an amount of at least 5% by weight, for example in an amount of from 5 to 50% by weight and in particular in an amount of from 5 to 20% by weight, based on the total weight of the composition.

Advantageously, the compositions according to the invention, in particular the aqueous active compound compositions, can be formulated as solvent-free or low-solvent compositions, i.e. the proportion of volatile components in the active compound composition is frequently not more than 10% by weight, in particular active compound composition is frequently not more than 10% by weight, in particular not more than 5% by weight and especially not more than 1% by weight, based on the total weight of the composition. Here, volatile components are those whose boiling point at atmospheric pressure is below 200° C.

A large number of different active compounds and effect substances can be formulated in the compositions according to the invention. A particular embodiment of the invention relates to the formulation of active compounds for crop protection, i.e. of herbicides, fungicides, nematicides, acaricides, insecticides and also active compounds which regulate plant growth.

Examples of fungicidally active compounds which can be formulated as active compound composition according to the invention include:
  acylalanines, such as benalaxyl, metalaxyl, ofurace, oxadixyl;
  amine derivatives, such as aldimorph, dodine, dodemorph, fenpropimorph, fenpropidin, guazatine, iminoctadine, spiroxamine, tridemorph;
  anilinopyrimidines, such as pyrimethanil, mepanipyrim or cyprodinil;
  antibiotics, such as cycloheximide, griseofulvin, kasugamycin, natamycin, polyoxin, streptomycin and validamycin A;
  azoles, such as bitertanol, bromoconazole, cyazofamid, cyproconazole, difenoconazole, dinitroconazole, epoxiconazole, etridiazole, fenbuconazole, fluquinconazole, flusilazole, flutriafol, fuberidazole, hexaconazole, hymexazole, imazalil, ipconazole, imibenconazole, metconazole, myclobutanil, penconazole, perfuazorate, propiconazole, prochloraz, prothioconazole, simeconazole, tebuconazole, tetraconazole, thiabendazole, triadimefon, triadimenol, triflumizole, triticonazole, 2-butoxy-6-iodo-3-propylchromen-4-one, N,N-dimethyl-3-(3-bromo-6-fluoro-2-methylindol-1-sulfonyl)-[1,2,4]triazole-1-sulfonamide;

2-methoxybenzophenones as described in EP-A 897904 by the formula I, for example metrafenone;
dicarboximides, such as iprodione, myclozolin, procymidone, vinclozolin;
dithiocarbamates, such as ferbam, nabam, maneb, mancozeb, metam, metiram, propineb, polycarbamate, thiram, ziram, zineb;
heterocyclic compounds, such as anilazine, benomyl, boscalid, carbendazim, carboxin, oxycarboxin, cyazofamid, dazomet, dithianon, ethirimol, dimethirimol, famoxadone, fenamidone, fenarimol, fuberidazole, flutolanil, furametpyr, isoprothiolane, mepronil, nuarimol, octhilinone, picobenzamid, probenazole, proquinazid, pyrifenox, pyroquilon, quinoxyfen, silthiofam, thiabendazole, thifluzamide, thiophanate-methyl, tiadinil, tricyclazole, triforine, 3-[5-(4-chlorophenyl)-2,3-dimethylisoxazolidin-3-yl]pyridine and bupirimate;
nitrophenyl derivatives, such as binapacryl, dinocap, dinobuton, nitrophthal-isopropyl;
phenylpyrroles, such as fenpiclonil and also fludioxonil;
fungicides not belonging to any of the other classes, such as acibenzolar-S-methyl, benthiavalicarb, carpropamid, chlorothalonil, cyflufenamid, cymoxanil, diclomezine, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzol, metrafenone, pencycuron, propamocarb, phthalide, toloclofosmethyl, quintozene, zoxamide, isoprothiolane, fluopicolide (picobenzamid); carpropamid, mandipropamid, N-(2-{4-[3-(4-chlorophenyl)prop-2-ynyloxy]-3-methoxyphenyl}ethyl)-2-methanesulfonylamino-3-methylbutyramide, N-(2-{4-[3-(4-chlorophenyl)prop-2-ynyloxy]-3-methoxyphenyl}ethyl)-2-ethanesulfonylamino-3-methylbutyramide; furametpyr, thifluzamide, penthiopyrad, fenhexamid, N-(2-cyanophenyl)-3,4-dichloroisothiazole-5-carboxamide, flubenthiavalicarb, methyl 3-(4-chlorophenyl)-3-(2-isopropoxycarbonylamino-3-methylbutyrylamino)propionate, methyl {2-chloro-5-[1-(6-methylpyridin-2-ylmethoxyimino)ethyl]benzyl}carbamate, methyl {2-chloro-5-[1-(3-methylbenzyloxyimino)ethyl]benzyl}carbamate, flusulfamide, amides of the formula

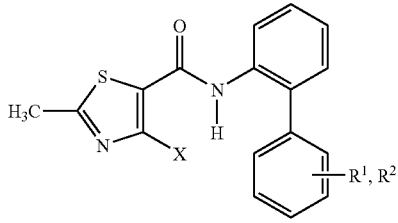

in which
X is $CHF_2$ or $CH_3$; and
$R^1$, $R^2$ independently of one another are halogen, methyl or halomethyl, for example $CF_3$;
strobilurins as described in WO 03/075663 by the general formula I, for example: azoxystrobin, dimoxystrobin, fluoxastrobin, kresoxim-methyl, metominostrobin, orysastrobin, picoxystrobin, pyraclostrobin and trifloxystrobin;
sulfenic acid derivatives, such as captafol, captan, dichlofluanid, folpet, tolylfluanid;
cinnamides and analogs thereof, such as dimethomorph, flumetover, flumorph;

6-aryl[1,2,4]triazolo[1,5-a]pyrimidines as described, for example, in WO 98/46608, WO 99/41255 or WO 03/004465 in each case by the formula I, e.g. 5-chloro-7-(4-methylpiperidin-1-yl)-6-(2,4,6-trifluorophenyl)-[1,2,4]triazolo[1,5-a]pyrimidine;
amide fungicides, such as cyclofenamid, and also (Z)-N-[α-(cyclopropylmethoxyimino)-2,3-difluoro-6-(difluoromethoxy)benzyl]-2-phenylacetamide.

Examples of herbicides which may be formulated as aqueous active compound compositions according to the invention include:
1,3,4-thiadiazoles, such as buthidazole and cyprazole;
amides, such as allidochlor, benzoylprop-ethyl, bromobutide, chlorthiamid, dimepiperate, dimethenamid, diphenamid, etobenzanid, flamprop-methyl, fosamine, isoxaben, metazachlor, monalide, naptalam, pronamide, propanil;
aminophosphoric acids, such as bilanafos, buminafos, glufosinate-ammonium, glyphosate, sulfosate;
aminotriazoles, such as amitrole,
anilides, such as anilofos; mefenacet;
aryloxyalkanoic acids, such as 2,4-D, 2,4-DB, clomeprop, dichlorprop, dichlorprop-P, fenoprop, fluoroxypyr, MCPA, MCPB, mecoprop, mecoprop-P, napropamide, napropanilide, triclopyr;
benzoic acids, such as chloramben, dicamba;
benzothiadiazinones, such as bentazone;
bleachers, such as clomazone, diflufenican, fluorochloridone, flupoxam, fluridone, pyrazolate, sulcotrione;
carbamates, such as carbetamide, chlorbufam, chlorpropham, desmedipham, phenmedipham, vernolate;
quinolinic acids, such as quinclorac, quinmerac;
dichloropropionic acids, such as dalapon;
dihydrobenzofurans, such as ethofumesate;
dihydrofuran-3-ones, such as flurtamone;
dinitroanilines, such as benefin, butralin, dinitramine, ethalfluralin, fluchloralin, isopropalin, nitralin, oryzalin, pendimethalin, prodiamine, profluralin, trifluralin;
dinitrophenols, such as bromofenoxim, dinoseb, dinoseb-acetate, dinoterb, DNOC, minoterb-acetate;
diphenyl ethers, such as acifluorfen-sodium, aclonifen, bifenox, chlornitrofen, difenoxuran, ethoxyfen, fluorodifen, fluoroglycofen-ethyl, fomesafen, furyloxyfen, lactofen, nitrofen, nitrofluorfen, oxyfluorfen;
dipyridyls, such as cyperquat, difenzoquat-methyl sulfate, diquat, paraquat-dichloride;
imidazoles, such as isocarbamid;
imidazolinones, such as imazamethapyr, imazapyr, imazaquin, imazethabenzmethyl, imazethapyr, imazapic, imazamox;
oxadiazoles, such as methazole, oxadiargyl, oxadiazon;
oxiranes, such as tridiphane;
phenols, such as bromoxynil, ioxynil;
phenoxyphenoxypropionic acid esters, such as clodinafop, cyhalofop-butyl, diclofop-methyl, fenoxaprop-ethyl, fenoxaprop-p-ethyl, fenthiaprop-ethyl, fluazifop-butyl, fluazifop-p-butyl, haloxyfop-ethoxyethyl, haloxyfop-methyl, haloxyfop-p-methyl, isoxapyrifop, propaquizafop, quizalofop-ethyl, quizalofop-p-ethyl, quizalofop-tefuryl;
phenylacetic acids, such as chlorfenac;
phenylpropionic acids, such as chlorophenprop-methyl;
ppi-active compounds, such as benzofenap, flumiclorac-pentyl, flumioxazin, flumipropyn, flupropacil, pyrazoxyfen, sulfentrazone, thidiazimin;
pyrazoles, such as nipyraclofen;

pyridazines, such as chloridazon, maleic hydrazide, norflurazon, pyridate;

pyridinecarboxylic acids, such as clopyralid, dithiopyr, picloram, thiazopyr;

pyrimidyl ethers, such as pyrithiobac-acid, pyrithiobac-sodium, KIH-2023, KIH-6127;

sulfonamides, such as flumetsulam, metosulam;

triazolecarboxamides, such as triazofenamide;

uracils, such as bromacil, lenacil, terbacil;

furthermore benazolin, benfuresate, bensulide, benzofluor, bentazon, butamifos, cafenstrole, chlorthal-dimethyl, cinmethylin, dichlobenil, endothall, fluorbentranil, mefluidide, perfluidone, piperophos, topramezone and prohexadione-calcium;

sulfonylureas, such as amidosulfuron, azimsulfuron, bensulfuron-methyl, chlorimuron-ethyl, chlorsulfuron, cinosulfuron, cyclosulfamuron, ethametsulfuron-methyl, flazasulfuron, halosulfuron-methyl, imazosulfuron, metsulfuron-methyl, nicosulfuron, primisulfuron, prosulfuron, pyrazosulfuron-ethyl, rimsulfuron, sulfometuron-methyl, thifensulfuron-methyl, triasulfuron, tribenuron-methyl, triflusulfuron-methyl, tritosulfuron;

crop protection agents of the cyclohexenone type, such as alloxydim, clethodim, cloproxydim, cycloxydim, sethoxydim and tralkoxydim. Very particularly preferred herbicidally active compounds of the cyclohexenone type are: tepraloxydim (cf. AGROW, No. 243, 11.3.95, page 21, caloxydim) and 2-(1-[2-{4-chlorophenoxy}propyloxyimino]butyl)-3-hydroxy-5-(2H-tetrahydrothiopyran-3-yl)-2-cyclohexen-1-one, and a very particularly preferred herbicidally active compound of the sulfonylurea type is: N-(((4-methoxy-6-[trifluoromethyl]-1,3,5-triazin-2-yl)amino)-carbonyl)-2-(trifluoromethyl)benzenesulfonamide.

Examples of insecticides which can be formulated as aqueous active compound composition according to the invention include:

organo(thio)phosphates, such as acephate, azamethiphos, azinphos-methyl, chlorpyrifos, chlorpyrifos-methyl, chlorfenvinphos, diazinon, dichlorphos, dimethylvinphos, dioxabenzofos, dicrotophos, dimethoate, disulfoton, ethion, EPN, fenitrothion, fenthion, isoxathion, malathion, methamidophos, methidathion, methyl-parathion, mevinphos, monocrotophos, oxydematon-methyl, paraoxon, parathion, phenthoate, phosalone, phosmet, phosphamidon, phorate, phoxim, pirimiphos-methyl, profenofos, prothiofos, primiphos-ethyl, pyraclofos, pyradaphenthion, sulprophos, triazophos, trichlorfon, tetrachlorvinphos, vamidothion;

carbamates, such as alanycarb, benfuracarb, bendiocarb, carbaryl, carbofuran, carbosulfan, fenoxycarb, furathiocarb, indoxacarb, methiocarb, methomyl, oxamyl, pirimicarb, propoxur, thiodicarb, triazamate;

pyrethroids, such as allethrin, bifenthrin, cyfluthrin, cyphenothrin, cyclopfothrin, cypermethrin, deltamethrin, esfenvalerate, ethofenprox, fenpropathrin, fenvalerate, cyhalothrin, lambda-cyhalothrin, imoprothrin, permethrin, prallethrin, pyrethrin I, pyrethrin II, silafluofen, tau-fluvalinate, tefluthrin, tralomethrin, transfluthrin, alpha-cypermethrin, zeta-cypermethrin, permethrin;

arthropod growth regulators: a) chitin synthesis inhibitors, for example benzoylureas, such as chlorfluazuron, cyromacin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists, such as halofenozide, methoxyfenozide, tebufenozide; c) juvenoids, such as pyriproxyfen, methoprene, fenoxycarb; d) lipid biosynthesis inhibitors, such as spirodiclofen;

neonicotinoids, such as flonicamid, clothianidin, dinotefuran, imidacloprid, thiamethoxam, nitenpyram, nithiazine, acetamiprid, thiacloprid;

Further insecticides which do not belong to the above classes, such as abamectin, acequinocyl, acetamiprid, amitraz, azadirachtin, bensultap, bifenazate, cartap, chlorfenapyr, chlordimeform, cyromazine, diafenthiuron, dinetofuran, diofenolan, emamectin, endosulfan, ethiprole, fenazaquin, fipronil, formetanate, formetanate hydrochloride, gamma-HCH, hydramethylnon, imidacloprid, indoxacarb, isoprocarb, metolcarb, pyridaben, pymetrozine, spinosad, tebufenpyrad, thiamethoxam, thiocyclam, pyridalyl, flonicamid, fluacypyrim, milbemectin, spiromesifen, flupyrazofos, NC 512, tolfenpyrad, flubendiamide, bistrifluoron, benclothiaz, pyrafluprole, pyriprole, amidoflumet, flufenerim, cyflumetofen, acequinocyl, lepimectin, profluthrin, dimefluthrin, amidrazone, metaflumizone, N-R'-2,2-dihalo-1-R"-cyclopropanecarboxamide-2-(2,6-dichloro-α, α,α-trifluoro-p-tolyl)hydrazone, N-R'-2,2-di(R''')propionamide-2-(2,6-dichloro-α,α,α-trifluoro-p-tolyl) hydrazone, where halo is chlorine or bromine, R' is methyl or ethyl, R" is hydrogen or methyl and R''' is methyl or ethyl, XMC and xylylcarb and also compounds of the formula below

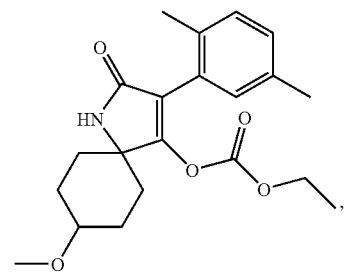, aminoisothiazoles of the formula

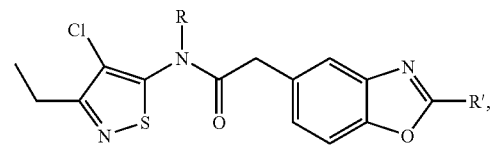, in which
R=—CH$_2$O—CH$_3$ or H and
R'=—CF$_2$CF$_2$CF$_3$;
anthranilamides of the formula

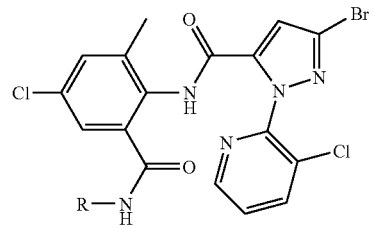

in which R is C$_1$-C$_4$-alkyl, such as methyl, ethyl, isopropyl or n-butyl,
and the compound of the formula below

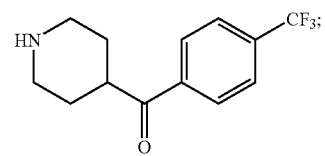

N-phenylsemicarbazones as described in EP-A 462 456 by the formula I, in particular compounds of the formula IV

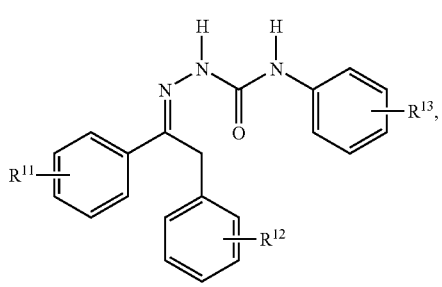

in which $R^{11}$ and $R^{12}$ independently of one another are hydrogen, halogen, CN, $C_1$-$C_4$-alkyl, $C_1$-$C_4$-alkoxy, $C_1$-$C_4$-haloalkyl or $C_1$-$C_4$-haloalkoxy and $R^{13}$ is $C_1$-$C_4$-alkyl, $C_1$-$C_4$-haloalkyl or $C_1$-$C_4$-haloalkoxy, for example compound IV in which $R^{11}$ is 3-$CF_3$ and $R^{12}$ is 4-CN and $R^{13}$ is 4-$OCF_3$ (=metaflumizone).

Useful growth coagulators are, for example, chlormequat-chloride, mepiquat-chloride, prohexadione-calcium or the group of the gibberellins. These include, for example, the gibberellins $GA_1$, $GA_3$, $GA_4$, $GA_5$ and $GA_7$, etc., and the corresponding exo-16,17-dihydrogibberellins, and also derivatives thereof, for example the esters with $C_1$-$C_4$-carboxylic acids. Preference according to the invention is given to exo-16,17-dihydro-$GA_5$ 13-acetate, furthermore 1-naphthylacetamide, 1-naphthylacetic acid, 2-naphthyloxyacetic acid, 3-CPA, 4-CPA, ancymidol, anthraquinone, BAP, butifos; tribufos, butralin, chlorflurenol, clofencet, cyclanilide, daminozide, dicamba, dikegulac sodium, dimethipin, chlorfenethol, etacelasil, ethephon, ethychlozate, fenoprop, 2,4,5-TP, fluoridamid, flurprimidol, flutriafol, guazatin, imazalil, indolylbutyric acid, indolylacetic acid, karetazan, kinetin, lactidichlor-ethyl, maleic hydrazide, mefluidide, naptalam, paclobutrazole, quinmerac, sintofen, tetcyclacis, thidiazuron, triiodobezoic acid, triapenthenol, triazethan, tribufos, trinexapac-ethyl and uniconazole.

A preferred embodiment of the invention relates to the use of the amphiphilic polymer compositions according to the invention for preparing aqueous active compound compositions of fungicides, in particular strobilurins, azoles and 6-aryltriazolo[1,5a]-pyrimidines as described, for example, in WO 98/46608, WO 99/41255 or WO 03/004465, in each case by the formula I, in particular for active compounds of the formula V

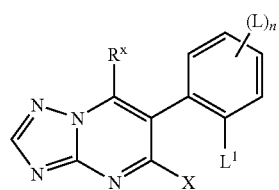

in which:
$R^x$ is a group $NR^{14}R^{15}$ or linear or branched $C_1$-$C_8$-alkyl which is optionally substituted by halogen, OH, $C_1$-$C_4$-alkoxy, phenyl or $C_3$-$C_6$-cycloalkyl, is $C_2$-$C_6$-alkenyl, $C_3$-$C_6$-cycloalkyl, $C_3$-$C_6$-cycloalkenyl, phenyl or naphthyl, where the 4 last-mentioned radicals may have 1, 2, 3 or 4 substituents selected from the group consisting of halogen, OH, $C_1$-$C_4$-alkyl, $C_1$-$C_4$-haloalkoxy, $C_1$-$C_4$-alkoxy and $C_1$-$C_4$-haloalkyl;

$R^{14}$, $R^{15}$ independently of one another are hydrogen, $C_1$-$C_8$-alkyl, $C_1$-$C_8$-haloalkyl, $C_3$-$C_{10}$-cycloalkyl, $C_3$-$C_6$-halocycloalkyl, $C_2$-$C_8$-alkenyl, $C_4$-$C_{10}$-alkadienyl, $C_2$-$C_8$-haloalkenyl, $C_3$-$C_6$-cycloalkenyl, $C_2$-$C_8$-halocycloalkenyl, $C_2$-$C_8$-alkynyl, $C_2$-$C_8$-haloalkynyl or $C_3$-$C_6$-cycloalkynyl, $R^{14}$ and $R^{15}$ together with the nitrogen atom to which they are attached are five- to eight-membered heterocyclyl which is attached via N and which may contain one, two or three further heteroatoms from the group consisting of O, N and S as ring members and/or may carry one or more substituents from the group consisting of halogen, $C_1$-$C_6$-alkyl, $C_1$-$C_6$-haloalkyl, $C_2$-$C_6$-alkenyl, $C_2$-$C_6$-haloalkenyl, $C_1$-$C_6$-alkoxy, $C_1$-$C_6$-haloalkoxy, $C_3$-$C_6$-alkenyloxy, $C_3$-$C_6$-haloalkenyloxy, (exo)-$C_1$-$C_6$-alkylene and oxy-$C_1$-$C_3$-alkyleneoxy;

L is selected from the group consisting of halogen, cyano, $C_1$-$C_6$-alkyl, $C_1$-$C_4$-haloalkyl, $C_1$-$C_6$-alkoxy, $C_1$-$C_4$-haloalkoxy and $C_1$-$C_6$-alkoxycarbonyl;

$L^1$ is halogen, $C_1$-$C_6$-alkyl or $C_1$-$C_6$-haloalkyl and in particular fluorine or chlorine;

X is halogen, $C_1$-$C_4$-alkyl, cyano, $C_1$-$C_4$-alkoxy or $C_1$-$C_4$-haloalkyl and preferably halogen or methyl and in particular chlorine.

Examples of compounds of formula V are
5-chloro-7-(4-methylpiperidin-1-yl)-6-(2,4,6-trifluorophenyl)-[1,2,4]triazolo-[1,5-a]pyrimidine,
5-chloro-7-(4-methylpiperazin-1-yl)-6-(2,4,6-trifluorophenyl)-[1,2,4]triazolo-[1,5-a]pyrimidine,
5-chloro-7-(morpholin-1-yl)-6-(2,4,6-trifluorophenyl)-[1,2,4]triazolo[1,5-a]pyrimidine,
5-chloro-7-(piperidin-1-yl)-6-(2,4,6-trifluorophenyl)-[1,2,4]triazolo[1,5-a]pyrimidine,
5-chloro-7-(morpholin-1-yl)-6-(2,4,6-trifluorophenyl)-[1,2,4]triazolo[1,5-a]pyrimidine,
5-chloro-7-(isopropylamino)-6-(2,4,6-trifluorophenyl)-[1,2,4]triazolo[1,5-a]pyrimidine,
5-chloro-7-(cyclopentylamino)-6-(2,4,6-trifluorophenyl)-[1,2,4]triazolo[1,5-a]pyrimidine,
5-chloro-7-(2,2,2-trifluoroethylamino)-6-(2,4,6-trifluorophenyl)-[1,2,4]triazolo[1,5-a]-pyrimidine,
5-chloro-7-(1,1,1-trifluoropropan-2-ylamino)-6-(2,4,6-trifluorophenyl)-[1,2,4]triazolo-[1,5-a]pyrimidine,
5-chloro-7-(3,3-dimethylbutan-2-ylamino)-6-(2,4,6-trifluorophenyl)-[1,2,4]triazolo-[1,5-a]pyrimidine,
5-chloro-7-(cyclohexylmethyl)-6-(2,4,6-trifluorophenyl)-[1,2,4]triazolo[1,5-a]pyrimidine,
5-chloro-7-(cyclohexyl)-6-(2,4,6-trifluorophenyl)-[1,2,4]triazolo[1,5-a]pyrimidine,
5-chloro-7-(2-methylbutan-3-yl)-6-(2,4,6-trifluorophenyl)-[1,2,4]triazolo[1,5-a]pyrimidine,
5-chloro-7-(3-methylpropan-1-yl)-6-(2,4,6-trifluorophenyl)-[1,2,4]triazolo-[1,5-a]pyrimidine,
5-chloro-7-(4-methylcyclohexan-1-yl)-6-(2,4,6-trifluorophenyl)-[1,2,4]triazolo-[1,5-a]pyrimidine,
5-chloro-7-(hexan-3-yl)-6-(2,4,6-trifluorophenyl)-[1,2,4]triazolo[1,5-a]pyrimidine,
5-chloro-7-(2-methylbutan-1-yl)-6-(2,4,6-trifluorophenyl)-[1,2,4]triazolo[1,5-a]pyrimidine,
5-chloro-7-(3-methylbutan-1-yl)-6-(2,4,6-trifluorophenyl)-[1,2,4]triazolo[1,5-a]pyrimidine,
5-chloro-7-(1-methylpropan-1-yl)-6-(2,4,6-trifluorophenyl)-[1,2,4]triazolo-[1,5-a]pyrimidine, 5-methyl-7-(4-methylpiperidin-1-yl)-6-(2,4,6-trifluorophenyl)-[1,2,4]triazolo[1,5-a]-pyrimidine,
5-methyl-7-(4-methylpiperazin-1-yl)-6-(2,4,6-trifluorophenyl)-[1,2,4]triazolo[1,5-a]-pyrimidine,
5-methyl-7-(morpholin-1-yl)-6-(2,4,6-trifluorophenyl)-[1,2,4]triazolo[1,5-a]pyrimidine,
5-methyl-7-(piperidin-1-yl)-6-(2,4,6-trifluorophenyl)-[1,2,4]triazolo[1,5-a]pyrimidine,
5-methyl-7-(morpholin-1-yl)-6-(2,4,6-trifluorophenyl)-[1,2,4]triazolo[1,5-a]pyrimidine,
5-methyl-7-(isopropylamino)-6-(2,4,6-trifluorophenyl)-[1,2,4]triazolo[1,5-a]pyrimidine,
5-methyl-7-(cyclopentylamino)-6-(2,4,6-trifluorophenyl)-[1,2,4]triazolo[1,5-a]pyrimidine,
5-methyl-7-(2,2,2-trifluoroethylamino)-6-(2,4,6-trifluorophenyl)-[1,2,4]triazolo[1,5-a]-pyrimidine,
5-methyl-7-(1,1,1-trifluoropropan-2-ylamino)-6-(2,4,6-trifluorophenyl)-[1,2,4]triazolo-[1,5-a]pyrimidine,
5-methyl-7-(3,3-dimethylbutan-2-ylamino)-6-(2,4,6-trifluorophenyl)-[1,2,4]triazolo-[1,5-a]pyrimidine,
5-methyl-7-(cyclohexylmethyl)-6-(2,4,6-trifluorophenyl)-[1,2,4]triazolo[1,5-a]pyrimidine,
5-methyl-7-(cyclohexyl)-6-(2,4,6-trifluorophenyl)-[1,2,4]triazolo[1,5-a]pyrimidine,
5-methyl-7-(2-methylbutan-3-yl)-6-(2,4,6-trifluorophenyl)-[1,2,4]triazolo[1,5-a]-pyrimidine,
5-methyl-7-(3-methylpropan-1-yl)-6-(2,4,6-trifluorophenyl)-[1,2,4]triazolo[1,5-a]-pyrimidine,
5-methyl-7-(4-methylcyclohexan-1-yl)-6-(2,4,6-trifluorophenyl)-[1,2,4]triazolo-[1,5-a]pyrimidine,
5-methyl-7-(hexan-3-yl)-6-(2,4,6-trifluorophenyl)-[1,2,4]triazolo[1,5-a]pyrimidine,
5-methyl-7-(2-methylbutan-1-yl)-6-(2,4,6-trifluorophenyl)-[1,2,4]triazolo[1,5-a]-pyrimidine,
5-methyl-7-(3-methylbutan-1-yl)-6-(2,4,6-trifluorophenyl)-[1,2,4]triazolo[1,5-a]pyrimidine and 5-methyl-7-(1-methylpropan-1-yl)-6-(2,4,6-trifluorophenyl)-[1,2,4]triazolo[1,5-a]-pyrimidine.

A further preferred embodiment of the invention relates to the use of the amphiphilic polymer compositions according to the invention for preparing active compound compositions, in particular aqueous active compound compositions, of insecticides, in particular of arylpyrroles, such as chlorfenapyr, of pyrethroids, such as bifenthrin, cyfluthrin, cycloprothrin, cypermethrin, deltamethrin, esfenvalerate, ethofenprox, fenpropathrin, fenvalerate, cyhalothrin, lambda-cyhalothrin, permethrin, silafluofen, taufluvalinate, tefluthrin, tralomethrin, alpha-cypermethrin, zeta-cypermethrin and permethrin, of neonicotinoids and of semicarbazones of the formula IV.

The amphiphilic polymer compositions according to the invention are furthermore suitable for preparing active compound compositions of pharmaceutically active compounds and prodrugs. These include benzodiazepines, antihypertensives, vitamins, cytostatics—especially taxol, anesthetics, neuroleptics, antidepressants, antibiotics, antimycotics, fungicides, chemotherapeutics, urologicals, platelet aggregation inhibitors, sulfonamides, spasmolytics, hormones, immunoglobulins, sera, thyroid therapeutics, psychopharmaceuticals, anti-Parkinson agents and other antihyperkinetics, opthalmologicals, neuropathy products, calcium metabolism regulators, muscle relaxants, anesthetics, lipid-lowering agents, hepatotherapeutics, coronary agents, cardiac agents, immunotherapeutics, regulatory peptides and their inhibitors, hypnotics, sedatives, gynecologicals, anti-gout agents, fibrinolytics, enzyme products and transport proteins, enzyme inhibitors, emetics, blood flow stimulators, diuretics, diagnostic aids, corticoids, cholinergics, bilary therapeutics, antiasthmatics, bronchospasmolytics, beta receptor blockers, calcium antagonists, ACE inhibitors, anti-arteriosclerotics, anti-inflammatory agents, anticoagulants, antihypotensives, antihypoglycemics, antihypertensives, antifibrinolytics, antiepileptics, anti-emetics, antidotes, antidiabetics, anti-arrhythmics, anti-anemics, anti-allergics, anthelmintics, analgesics, analeptics, aldosterone antagonists, and slimming products. Examples of suitable pharmaceutically active compounds are in particular the active compounds mentioned in paragraphs 0105 to 0131 of US 2003/0157170.

Furthermore, the amphiphilic polymer compositions according to the invention are suitable for preparing aqueous preparations of cosmetically active compounds, in particular of cosmetic oils and fats, such as peanut oil, jojoba oil, coconut oil, almond oil, olive oil, palm oil, castor oil; soybean oil or wheat germ oil, essential oils, such as dwarf pine oil, lavender oil, rosemary oil, fir needle oil, pine needle oil, eucalyptus oil, peppermint oil, sage oil, bergamot oil, terpentine oil, melissa oil, juniper berry oil, lemon oil, anise oil, cardamom oil, camphor oil, etc., or mixtures of these oils.

Moreover, the amphiphilic polymer compositions according to the invention are suitable for preparing preparations, in particular aqueous preparations, of food additives, such as water-insoluble vitamins and provitamins, such as vitamin A, vitamin A acetate, vitamin D, vitamin E, tocopherol derivatives, such as tocopherol acetate, and vitamin K.

Examples of effect substances which can be formulated as active compound compositions according to the invention are:

Dyes: for example the dyes described in DE-A 10245209 and the compounds which, according to the Color Index, are referred to as disperse dyes and solvent dyes and which are also called dispersion dyes. A compilation of suitable dispersion dyes can be found, for example, in Ullmanns Enzyklopädie der technischen Chemie [Ullmann's Encyclopedia of Industrial Chemistry], 4th edition, Vol. 10, pp. 155-165 (see also Vol. 7, p. 585ff.—anthraquinone dyes; Vol. 8, p. 244ff.—azo dyes; Vol. 9, p. 313ff.—quinophthalone dyes). This literature reference and the compounds mentioned therein are expressly incorporated herein by way of reference. Dispersion dyes and solvent dyes which are suitable according to the invention include very different classes of dyes with different chromophores, for example anthraquinone dyes, monoazo and diazo dyes, quinophthalones, methyne and azomethyne dyes, naphthalimide dyes, naphthoquinone dyes and nitro dyes. Examples of dispersion dyes which are suitable according to the invention are the dispersion dyes of the following Color Index list: C.I. Disperse Yellow 1-228, C.I. Disperse Orange 1-148, C.I. Disperse Red 1-349, C.I. Disperse Violet 1-97, C.I. Disperse Blue 1-349, C.I. Disperse Green 1-9, C.I. Disperse Brown 1-21, C.I. Disperse Black 1-36. Examples of solvent dyes which are suitable according to the invention are the compounds of the following Color Index list: C.I. Solvent Yellow 2-191, C.I. Solvent Orange 1-113, C.I. Solvent Red 1-248, C.I. Solvent Violet 2-61, C.I. Solvent Blue 2-143, C.I. Solvent Green 1-35, C.I. Solvent Brown 1-63, C.I. Solvent Black 3-50. Other dyes which are suitable according to the invention are derivatives of naphthalene, anthracene, perylene, terylene, quarterylene, and also diketopyrrolopyrrole dyes, perinone dyes, cumarin dyes, isoindoline and isoindolinone dyes, porphyrin dyes, phthalocyanine and naphthalocyanine dyes; and UV absorbers: in particular compounds from groups a to g mentioned below.

a) 4,4-diarylbutadienes,
b) cinnamic esters,
c) benzotriazoles,
d) hydroxybenzophenones,
e) diphenylcyanoacrylates,
f) oxamides,
g) 2-phenyl-1,3,5-triazines;

Group a) of the 4,4-diarylbutadienes includes, for example, compounds of the formula A.

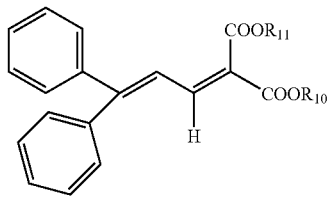

The compounds are known from EP-A-916 335. The substituents $R_{10}$ and/or $R_{11}$ are preferably $C_1$-$C_8$-alkyl and $C_5$-$C_8$-cycloalkyl.

Group b) of the cinnamic esters includes, for example, 2-isoamyl 4-methoxycinnamate, 2-ethylhexyl 4-methoxycinnamate, methyl α-methoxycarbonylcinnamate, methyl α-cyano-β-methyl-p-methoxycinnamate, butyl α-cyano-β-methyl-p-methoxycinnamate and methyl α-methoxycarbonyl-p-methoxycinnamate.

Group c) of the benzotriazoles includes, for example, 2-(2'-hydroxyphenyl)benzotriazoles, such as 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-ylphenol]; the product of the esterification of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$]$_2$, where R=3'-tert-butyl-4'-hydroxy-5'-2H-benzotriazol-2-ylphenyl, and mixtures thereof.

Group d) of the hydroxybenzophenones includes, for example, 2-hydroxybenzophenones, such as 2-hydroxy-4-methoxybenzophenone, 2,2'-dihydroxy-4-methoxybenzophenone, 2,4-dihydroxybenzophenone, 2,2',4,4'-tetrahydroxybenzophenone, 2,2'-dihydroxy-4,4'-dimethoxybenzophenone, 2,2'-dihydroxy-4,4'-dimethoxybenzophenone, 2-hydroxy-4-(2-ethylhexyloxy)benzophenone, 2-hydroxy-4-(n-octyloxy)benzophenone, 2-hydroxy-4-methoxy-4'-methylbenzophenone, 2-hydroxy-3-carboxybenzophenone, 2-hydroxy-4-methoxybenzophenone-5-sulfonic acid and its sodium salt, 2,2'-dihydroxy-4,4'-dimethoxybenzophenone-5,5'-bissulfonic acid and its sodium salt.

Group e) of the diphenylcyanoacrylates includes, for example, ethyl 2-cyano-3,3-diphenylacrylate, which is commercially available, for example, under the name Uvinul® 3035 from BASF AG, Ludwigshafen, 2-ethylhexyl 2-cyano-3,3-diphenylacrylate, which is commercially available, for example, as Uvinul® 3039 from BASF AG, Ludwigshafen, and 1,3-bis[(2'-cyano-3',3'-diphenylacryloyl)oxy]-2,2-bis{[2'-cyano-3',3'-diphenylacryloyl)oxy]methyl}propane, which is commercially available, for example, under the name Uvinul® 3030 from BASF AG, Ludwigshafen.

Group f) of the oxamides includes, for example, 4,4'-dioctyloxyoxanilide, 2,2'-di-ethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, and also mixtures of ortho-, para-methoxy-disubstituted oxanilides and mixtures of ortho- and para-ethoxy-disubstituted oxanilides.

Group g) of the 2-phenyl-1,3,5-triazines includes, for example, 2-(2-hydroxyphenyl)-1,3,5-triazines, such as 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-di-hydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropoxy)-phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxyphenyl)-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine and 2-(2-hydroxyphenyl)-4-(4-methoxyphenyl)-6-phenyl-1,3,5-triazine.

In addition to the components mentioned above, the aqueous active compound compositions according to the invention may also comprise conventional surface-active substances and other additives. The surface-active substances include surfactants, dispersants and wetting agents. The other additives include in particular thickeners, antifoams, preservatives, antifreeze agents, stabilizers, etc.

Suitable in principle are anionic, cationic, nonionic and amphoteric surfactants, which includes polymer surfactants and surfactants having heteroatoms in the hydrophobic group.

The anionic surfactants include, for example, carboxylates, in particular alkali metal, alkaline earth metal and ammonium salts of fatty acids, for example potassium stearate, which are usually also referred to as soaps; acyl glutamates; sarcosinates, for example sodium lauroyl sarcosinate; taurates; methylcelluloses; alkyl phosphates, in particular alkyl esters of mono- and diphosphoric acid; sulfates, in particular alkyl sulfates and alkyl ether sulfates; sulfonates, furthermore alkylsulfonates and alkylarylsulfonates, in particular alkali metal, alkaline earth metal and ammonium salts of arylsulfonic acids and of alkyl-substituted arylsulfonic acids, alkylbenzenesulfonic acids, such as, for example, ligno- and phenolsulfonic acid, naphthalene- and dibutyl-naphthalenesulfonic acids, or dodecylbenzenesulfonates, alkylnaphthalenesulfonates, alkyl methyl ester sulfonates, condensates of sulfonated naphthalene and derivatives thereof with formaldehyde, condensates of naphthalenesulfonic acids, phenol- and/or phenolsulfonic acids with formaldehyde or with formaldehyde and urea, mono- or dialkyl sulfosuccinates; and also protein hydrolyzates and lignosulfite waste liquors. The abovementioned sulfonic acids are advantageously used in the form of their neutral or, if appropriate, basic salts.

The cationic surfactants include, for example, quaternized ammonium compounds, in particular alkyltrimethylammonium halides, dialkyldimethylammonium halides, alkyltrimethylammonium alkyl sulfates, dialkyldimethylammonium alkyl sulfates, and also pyridine and imidazoline derivatives, in particular alkylpyridinium halides.

The nonionic surfactants include, for example:
fatty alcohol polyoxyethylene esters, for example lauryl alcohol polyoxyethylene ether acetate,
alkyl polyoxyethylene ethers and alkyl polyoxypropylene ethers, for example of isotridecyl alcohol, and fatty alcohol polyoxyethylene ethers,
alkylaryl alcohol polyoxyethylene ethers, for example octylphenol polyoxyethylene ether,
alkoxylated animal and/or vegetable fats and/or oils, for example corn oil ethoxylates, castor oil ethoxylates, tallow fat ethoxylates,
glycerol esters, such as, for example, glycerol monostearate,
fatty alcohol alkoxylates and oxoalcohol alkoxylates, in particular of the type RO—$(R_{18}O)_r(R_{19}O)_sR_{20}$ where $R_{18}$ and $R_{19}$ independently of one another=$C_2H_4$, $C_3H_6$, $C_4H_8$ and $R_{20}$=H, or $C_1$-$C_{12}$-alkyl, R=$C_3$-$C_{30}$-alkyl or $C_6$-$C_{30}$-alkenyl, r and s independently of one another are 0 to 50, where one of these must be other than 0, such as isotridecyl alcohol and oleyl alcohol polyoxyethylene ether,
alkylphenol alkoxylates, such as, for example, ethoxylated isooctylphenol, octylphenol or nonylphenol, tributylphenol polyoxyethylene ether,
fatty amine alkoxylates, fatty acid amide alkoxylates and fatty acid diethanolamide alkoxylates, in particular their ethoxylates,
sugar surfactants, sorbitol esters, such as, for example, sorbitan fatty acid esters (sorbitan monooleate, sorbitan tristearate), polyoxyethylene sorbitan fatty acid esters, alkyl polyglycosides, N-alkylgluconamides,
alkyl methyl sulfoxides,
alkyldimethylphosphine oxides, such as, for example, tetradecyldimethylphosphine oxide.

The amphoteric surfactants include, for example, sulfobetaines, carboxybetaines and alkyldimethylamine oxides, for example tetradecyldimethylamine oxide.

Other surfactants which may be mentioned here by way of example are perfluorosurfactants, silicone surfactants, phospholipids, such as, for example, lecithin or chemically modified lecithins, amino acid surfactants, for example N-lauroylglutamate.

Unless specified otherwise, the alkyl chains of the surfactants listed above are linear or branched radicals having usually 8 to 20 carbon atoms.

In one embodiment, the aqueous active compound composition according to the invention comprises not more than 10% by weight, preferably not more than 5% by weight and in particular not more than 3% by weight, for example from 0.01 to 5% by weight or from 0.1 to 3% by weight, of conventional surface-active substances, in each case based on the total amount of active compound and polymer composition. In this case, the conventional surface-active substances preferably do not constitute more than 5% by weight and in particular not more than 3% by weight, for example from 0.01 to 5% by weight or from 0.1 to 3% by weight, based on the total weight of the composition.

However, depending on the application, it may be advantageous to formulate the active compound compositions according to the invention with surface-active substance. In this case, the proportion of conventional surface-active substances is frequently in the range from 0.5 to 30% by weight, in particular in the range from 1 to 20% by weight, based on the total amount of active compound and polymer composition, or in the range from 0.2 to 20% by weight and in particular in the range from 0.5 to 15% by weight, based on the total weight of the formulated composition.

In spite of the fact that one of the advantages of the compositions according to the invention is their low content of volatile organic compounds, for some applications it may be desirable for the compositions according to the invention to be mixed with organic solvents, oils and fats, preferably solvents or oils and fats which are environmentally friendly or biocompatible, for example the water-miscible solvents mentioned above or solvents, oils or fats whose miscibility with water is only very limited, or which are not miscible with water, for example, with:

paraffin oils, aromatic hydrocarbons and mixtures of aromatic hydrocarbons, for example xylenes, Solvesso 100, 150 or 200, and the like,
phenols and alkylphenols. for example phenol, hydroquinone, nonylphenol, etc.
ketones having more than 4 carbon atoms, such as cyclohexanone, isophorone, isopherone, acetophenone, acetonaphthone,
alcohols having more than 4 carbon atoms, such as acetylated lanolin alcohol, cetyl alcohol, 1-decanol, 1-heptanol, 1-hexanol, isooctadecanol, isopropyl alcohol, oleyl alcohol, benzyl alcohol,
carboxylic esters, for example dialkyl adipates, such as bis(2-ethylhexyl) adipate, dialkyl phthalates, such as bis (2-ethylhexyl) phthalate, alkyl acetates (also branched alkyl groups), such as ethyl acetate and ethyl acetoacetate, stearates, such as butyl stearate, glycerol monostearate, citrates, such as acetyltributyl citrate, furthermore cetyl octanoate, methyl oleate, methyl p-hydroxybenzoate, methyl tetradecanoate, propyl p-hydroxybenzoate, methyl benzoates, lactates, such as isopropyl lactates, butyl lactate and 2-ethylhexyl lactate,
vegetable oils, such as palm oil, rapeseed oil, castor oil and derivatives thereof, such as, for example, oxidized, coconut oil, cod liver oil, corn oil, soybean oil, linseed oil, olive oil, peanut oil, safflower oil, sesame oil, grapefruit oil, basil oil, apricot oil, ginger oil, geranium oil, orange oil, rosemary oil, macadamia oil, onion oil, mandarin oil, pine oil, sunflower oil,
hydrogenated vegetable oils, such as hydrogenated palm oil, hydrogenated rapeseed oil, hydrogenated soybean oil,
animal oils, such as pig fat oil, fish oils,
dialkylamides of medium- to long-chain fatty acids, for example Hallcomides, and also
vegetable oil esters, such as rapeseed oil methyl ester.

Suitable thickeners are compounds which confer a pseudoplastic flow behavior to the formulation, i.e. high viscosity at rest and low viscosity in the agitated state. Mention may be made, in this connection, for example, of polysaccharides or organic sheet minerals, such as Xanthan Gum® (Keizan® from Kelco), Rhodopol® 23 (Rhone Poulenc) or Veegum® (from R. T. Vanderbilt) or Attaclay® (from Engelhardt), Xanthan Gum® being preferred.

Antifoam agents suitable for the dispersions according to the invention are, for example, silicone emulsions (such as, for example, Silikon® SRE, from Wacker, or Rhodorsil® from Rhodia), long-chain alcohols, fatty acids, organofluorine compounds and mixtures thereof.

Bactericides can be added to stabilize the compositions according to the invention against attack by microorganisms. Suitable bactericides are, for example, Proxel® from ICI or Acticide® RS from Thor Chemie and Kathon® MK from Rohm & Haas.

Suitable antifreeze agents are organic polyols, for example ethylene glycol, propylene glycol or glycerol. These are usually employed in amounts of not more than 10% by weight, based on the total weight of the active compound composition, so that the desired content of volatile compounds is not exceeded. In one embodiment of the invention, the proportion of volatile organic compounds different therefrom is preferably not more than 1% by weight, in particular not more than 1000 ppm.

If appropriate, the active compound compositions according to the invention may comprise 1 to 5% by weight of buffer, based on the total amount of the formulation prepared, to regulate the pH, the amount and type of buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Depending on the nature of the active compound or effect substance comprised therein, the active compound compositions or effect substance compositions according to the invention can be used in a manner comparable per se to conventional formulations of the respective active compound or effect substance. For example, active compound compositions comprising at least one insecticidally, acaricidally or nematocidally active compound can be used for controlling harmful insects, acarids or nematodes. If the active compound compositions according to the invention comprise at least one fungicidally active compound, they can be used for controlling harmful fungi. If the active compound compositions according to the invention comprise a herbicidally active compound, they can be used for controlling weed grasses and the like.

Depending on the nature of the active compound, the compositions according to the invention are used in particular for protecting plants against attack by harmful organisms such as insects, acarina, nematodes, or for protection against attack by phytopathogenic fungi and the like, or for the treatment of seed or in the protection of materials, for example for protecting lignocellulose materials, such as wood, against attack by harmful insects, such as wood-destroying beetles, termites, ants and the like, or against attack by wood-discoloring or wood-destroying fungi.

The compositions according to the invention can, of course, also be employed in cosmetics or in medicine or in industrial applications.

The invention is now illustrated in more detail using the examples below.

I. PREPARATION OF THE AMPHIPHILIC POLYMER COMPOSITION

I.1 Preparation Example 1

1444 g of tetrahydrofuran were heated under reflux. Over a period of 2 hours, feed 1a, consisting of 2109 g of methyl methacrylate and 703 g of styrene, and feed 1b, consisting of 1444 g of tetrahydrofuran (THF), 18.6 g of azobisisobutyronitrile (AIBN) and 58.4 g of mercaptoethanol, were added simultaneously, and the mixture was kept under reflux for 24 h. 430 g of a commercially available biuret of hexamethylene diisocyanate (NCO content 22%, viscosity at 23° C. of 4.0 Pa·s) and 0.1 g of dibutyltin dilaurate were then added, and the reaction mixture was stirred at the same temperature until the NCO content of the mixture had fallen to 1.02%. 3000 g of a methyl-terminated polyethylene oxide (number-average molecular weight 2000 dalton, KOH number 33 mg/g of solid substance) were then added to the mixture, and the reaction mixture was stirred at the same temperature until the NCO content was 0° C. Over a period of 30 min, 14.7 kg of water were then added and tetrahydrofuran was distilled off under reduced pressure. This gave a 30% by weight strength aqueous dispersion of the amphiphilic polymer composition having a mean particle size of 50 nm (determined by dynamic light scattering).

I.2 Preparation Example 2

1444 g of THF were heated under reflux. Over a period of 2 hours, feed 1a, consisting of 2109 g of methyl methacrylate and 703 g of styrene, and feed 1b, consisting of 1444 g of tetrahydrofuran, 18.6 g of AIBN and 58.4 g of mercaptoethanol, were added simultaneously, and the mixture was kept under reflux for 24 h. 167 g of a isophorone diisocyanate and 0.7 g of dibutyltin dilaurate were then added, and the reaction mixture was stirred at the same temperature until the NCO content of the mixture had fallen to 0.53%. 1500 g of a methyl-terminated polyethylene oxide (number-average molecular weight 2000 dalton, KOH number 33 mg/g of solid substance) were then added to the mixture, and the reaction mixture was stirred at the same temperature until the NCO content was 0° C. Over a period of 30 min, 10.6 kg of water were then added and tetrahydrofuran was distilled off under reduced pressure. This gave a 30% by weight strength aqueous dispersion of the amphiphilic polymer composition having a mean particle size of 52 nm (determined by dynamic light scattering).

I.3 Preparation Example 3

1444 g of THF were heated under reflux. Over a period of 2 hours, feed 1a, consisting of 2109 g of methyl methacrylate and 703 g of styrene, and feed 1b, consisting of 1444 g of tetrahydrofuran, 18.6 g of AIBN and 58.4 g of mercaptoethanol, were added simultaneously, and the mixture was kept under reflux for 24 h. 430 g of a commercially available biuret of hexamethylene diisocyanate (NCO content 22%, viscosity at 23° C. 4.0 Pa·s), 3000 g of a methyl-terminated polyethylene oxide (number-average molecular weight 2000 dalton, KOH number 33 mg/kg of solid substance) and 0.87 g of dibutyltin dilaurate were then added and the reaction mixture was stirred at the same temperature until the NCO content was 0%. Over a period of 30 min, 14.7 kg of water were then added and tetrahydrofuran was distilled off under reduced pressure. This gave a 30% by weight strength aqueous dispersion of the amphiphilic polymer composition having a mean particle size of 52 nm (determined by dynamic light scattering).

I.4 Preparation Example 4

430 g of the commercially available biuret of hexamethylene diisocyanate used in preparation example 1, 3000 g of a methyl-terminated polyethylene oxide (OH number 33 mg of KOH/g of solid substance) and 117 mg of dibutyltin dilaurate were dissolved in 3430 g of tetrahydrofuran. The solution was stirred at reflux temperature until the NCO content was 0.46%.

1444 g of THF were heated under reflux. Over a period of 2 hours, feed 1a, consisting of 2109 g of methyl methacrylate and 703 g of styrene, and feed 1b, consisting of 1444 g of tetrahydrofuran, 18.6 g of AIBN and 58.4 g of mercaptoethanol, were added simultaneously, and the mixture was kept under reflux for 24 h. The reaction product, which had been prepared in the meantime, of the biuret of the hexamethylene diisocyanate with a methyl-terminated polyethylene oxide was then added, and the reaction mixture was stirred at the same temperature until the NCO content was 0%. Over a period of 30 min, 14.7 kg of water were then added and tetrahydrofuran was distilled off under reduced pressure. This gave a 30% strength aqueous dispersion of the amphiphilic polymer composition (particle size 129 nm, measured using dynamic light scattering).

II. PREPARATION OF AQUEOUS ACTIVE COMPOUND PREPARATIONS ACCORDING TO THE INVENTION

II.1 Analysis

The viscosities stated here were determined in a rotation viscometer according to DIN 53019-2.

The mean particle diameters were determined by the method of static light scattering using a dilute sample of the aqueous active compound formulation at 20° C.

To test the storage stability, the aqueous active compound compositions were stored at 54° C. for 2 weeks and at 5° C. for 2 weeks. Moreover, the active compound compositions were frozen and thawed. The samples are storage-stable if neither sedimentation nor creaming is observed under these conditions.

II.2 General Preparation Procedures

1. Solubilization method (liquid active compounds and active compound melts):
   10 g of active compound are stirred into 90 g of an aqueous dispersion of an amphiphilic polymer composition comprising 30 g of polymer, at a temperature at which the active compound is present as a low-viscosity melt. Depending on the viscosity of the polymer solution and the active compound melt, stirring is carried out using a magnetic stirrer or an Ultraturrax. The time required until the solubilization equilibrium is reached depends on the polymer composition and on the active compound and can be a few seconds, but also a number of hours. The solubilization equilibrium is reached when the active compound is uniformly distributed in the mixture and no change of particle size is observed even when more energy is introduced.

2. Phase inversion method:
   10 g of the liquid or solid active compound and 30 g of the amphiphilic polymer composition (polymer content >95% by weight) are dissolved in an organic solvent which has a boiling point of below 100° C. (for example tetrahydrofuran). Water is then added with stirring, and the organic solvent is subsequently removed by distillation. The amount of water added is such that the resulting aqueous formulation comprises 10% by weight of active compound and 30% by weight of polymer.

3. Method of solid solution:
   0.5 g of the amphiphilic polymer composition (polymer content >95% by weight) and 0.1 g of the active compound are dissolved in about 20 ml of dimethylformamide. The solvent is then removed completely (for example on a rotary evaporator), so that a solid solution of hydrophobic active compound and amphiphilic polymer composition remains. A buffered aqueous solution (100 ml, pH 6.8) is added, and the mixture is stirred for 24 hours. After filtration, the solution is analyzed by HPLC (UV detector), and the active compound concentration is determined.

4. Nozzle precipitation:
   Using two pumps, a 30% strength aqueous polymer dispersion and a 40% strength active compound/THF solution are mixed in a mixing apparatus via a mixing nozzle. The flow rate of the polymer dispersion is 12 kg/h, the flow rate of the THF solution is 3 kg/h, so that the total flow rate is 15 kg/h. The mixing apparatus is comparable to the apparatus described in "Handbook of Industrial Crystallization" (A. S. Myerson, 1993 Butterworth-Heinemann, page 139, ISBN 0-7506-9155-7). This gave a light-yellow milky suspension comprising 8% of active compound and 24% of polymer. The THF and some of the water are then removed by distillation, so that an aqueous nanoparticulate formulation comprising 10% of active compound and 30% of polymer is formed.

II.3 Formulation Example 1

Solubilization of Pyraclostrobin by the Phase Inversion Method (General Procedures 2)

Together, 10 g of pyraclostrobin and 30 g of amphiphilic polymer composition from example 2 were dissolved in 100 g of THF. With stirring, water was then added and the THF was removed under reduced pressure. The amount of water was chosen such that the resulting aqueous formulation comprised 10% by weight of active compound and 30% by weight of the amphiphilic polymer composition.

The resulting active compound composition was homogeneous, virtually visually transparent, sedimentation-stable for at least several months and could be diluted with water (both with deionized water and water 10°d [German hardness]) without any sedimentation or crystallization of the active compound taking place. The disperse phase (polymer/active compound particle) had a spherical structure and a mean diameter, determined by light scattering, of about 30 nm.

II.4 Formulation Example 2

Solubilization of Pyraclostrobin by the Solubilization Method (General Procedure 1)

At 70° C., pyraclostrobin is a readily flowing melt (viscosity 2200 mPas), and accordingly was formulated at a temperature of 70° C. using the general procedure 1. The resulting active compound composition was homogeneous, virtually visually transparent, sedimentation-stable for at least several months and could be diluted with water (both with deionized water and water 10°d) without any sedimentation or crystallization of the active compound taking place.

The disperse phase (polymer/active compound particle) had a spherical structure and a mean diameter, determined by light scattering, of about 30 nm.

II.5 Formulation Example 3

Solubilization of Pyraclostrobin by Nozzle Precipitation (General Procedure 4)

Pyraclostrobin was formulated using the general procedure 4. The resulting active compound composition was homogeneous, virtually visually transparent, sedimentation-stable for at least several months and could be diluted with water (both with deionized water and water 10°d) without any sedimentation or crystallization of the active compound taking place.

II.6 Formulation Example 4

Solubilization of Metconazole by the Phase Inversion Method (General Procedure 2)

Together, 10 g of metconazole, a solid having a melting point of from 110 to 113° C., and 30 g of amphiphilic polymer composition from example 1 were dissolved in 100 g of THF. With stirring, water was then added and the THF was removed under reduced pressure. The amount of water was chosen such that the resulting aqueous formulation-comprised 10% by weight of active compound and 30% by weight of the amphiphilic polymer composition.

The resulting active compound composition was homogeneous, virtually visually transparent, sedimentation-stable for at least several months and could be diluted with water (both with deionized water and water 10°d) without any sedimentation or crystallization of the active compound taking place. The disperse phase (polymer/active compound particle) had a spherical structure and a mean diameter, determined by light scattering, of about 30 nm.

The other active compounds listed in table 1 can also be formulated in an analogous manner.

TABLE 1

| Active compound | Solubility in distilled water [mg/l] |
|---|---|
| epoxyconazole | 6.63 |
| boscalid | 4.6 |
| pyraclostrobin | 2.4 |
| metconazole | 15 |
| alpha-cypermethrin | 0.01 |

II.7 Formulation Example 5

Solubilization of Vitamin A Acetate by the Phase Inversion Method of (General Procedure 2)

Together, 10 g of vitamin A acetate and 30 g of amphiphilic polymer composition from example 1 were dissolved in 100 g of THF. With stirring, water was then added and the THF was removed under reduced pressure. The amount of water was chosen such that the resulting aqueous formulation comprised 10% by weight of active compound and 30% by weight of the amphiphilic polymer composition.

The resulting active compound composition was homogeneous, virtually visually transparent, sedimentation-stable for at least several months and could be diluted with water (both with deionized water and water 10°d) without any sedimentation or crystallization of the active compound taking place.

III. APPLICATION TEST

III.1 Assessment of the Fungicidal Activity

The aqueous active compound composition from formulation example 1 and two commercial formulations of the same active compound pyraclostrobin were compared with respect to their activity against *Phytophthora infestans* on tomatoes in a greenhouse according to the following procedure (prevention test, protective activity):

Using tap water, the active compound formulations were diluted to the desired active compound concentrations (between 4 and 250 ppm). The application to tomato plants was carried out using a spray cabin having a volume of 25 ml, which corresponds to an amount of water of about 500 l/ha, which is customary in practice. The standard fungus (*Phytophthora infestans*) was inoculated 7 days after the treatment. The test plants were placed in a greenhouse at from 18 to 20° C. and 90% relative atmospheric humidity. Assessment was carried out 5 days after the inoculation, by determining the infection of the leaves in percent.

The results of the biological test are summarized in table 2. The results show that the fungicidal activity of the active compound stabilized in the polymer particles is on the same level as that of commercial products.

TABLE 2

*Phytophthora infestans* - infection [%] on tomatoes after five days, as a function of the active compound content

| Application rate [mg] | Infection [%] Formulation example 1 | Infection [%] Commercial product [1] |
|---|---|---|
| 250 | 0 | 0 |
| 63 | 0 | 0 |
| 16 | 0 | 0 |
| 4 | 3 | 4 |
| 1 | 30 | 50 |

[1] EC formulation
23.5% by weight of pyraclostrobin,
4.7% by weight of anionic wetting agent and
4.7% by weight of nonionic wetting agent in
67.1% by weight of an aromatic solvent

We claim:

1. An amphiphilic polymer composition, obtainable by reacting
    a) at least one hydrophobic polymer P1 which carries functional groups $R^{P1}$ which are reactive toward isocyanate groups and which is constructed of ethylenically unsaturated monomers M1, comprising:
        a1) at least 10% by weight, based on the total amount of monomers M1, of monomers M1a of the formula I

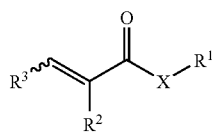

(I)

in which X is oxygen or a group N—$R^4$;
$R^1$ is $C_1$-$C_{10}$-alkyl, $C_5$-$C_{10}$-cycloalkyl, phenyl or phenyl-$C_1$-$C_4$-alkyl;
$R^2$ is hydrogen or $C_1$-$C_4$-alkyl;
$R^3$ is hydrogen or $C_1$-$C_4$-alkyl; and
$R_4$ is hydrogen or $C_1$-$C_4$-alkyl;

a2) up to 90% by weight, based on the total amount of monomers M1, of neutral monoethylenically unsaturated monomers M1b whose solubility in water at 25° C. is less than 50 g/l and which are different from the monomers M1a, wherein the total amount of M1a and M1b is at least 80% by weight based on the total amount of monomers M1, and a3) not more than 20% by weight, based on the total amount of monomers M1, of ethylenically unsaturated monomers M1c which are different from the monomers M1a and M1b, b) at least one hydrophilic polymer P2 which carries functional groups $R^{P2}$ which are reactive toward isocyanate groups, wherein the polymer P2 is an aliphatic polyether, at least 50% by weight of which is constructed from ethylene oxide groups, and has no ionic groups, c) with at least one compound V which contains isocyanate groups and, with respect to the isocyanate groups, has a functionality of at least 1.5, where the proportion of the hydrophobic polymer P1 in the amphiphilic polymer composition is from 20 to 68% by weight, the proportion of the hydrophilic polymer P2 in the amphiphilic polymer composition is from 30 to 78% by weight and the proportion of the compound V in the amphiphilic polymer composition is from 2 to 20% by weight, in each case based on the total weight of polymer P1, polymer P2 and compound V.

2. The polymer composition according to claim 1 in which the hydrophobic polymer has, with respect to the functional groups $R^{P1}$, a functionality F1 in the range from 0.5 to 1.5.

3. The polymer composition according to claim 1 in which the hydrophobic polymer P1 has a number-average molecular weight in the range from 500 to 20,000 dalton.

4. The polymer composition according to claim 1 in which the hydrophilic polymer P2 is an aliphatic polyether, at least 70% by weight of which is constructed from ethylene oxide groups.

5. The polymer composition according to claim 1 in which the hydrophilic polymer P2 has, with respect to the functional groups $R^{P2}$, a functionality F2 in the range from 0.5 to 3.0.

6. The polymer composition according to claim 1 in which the hydrophilic polymer P2 has a number-average molecular weight in the range from 500 to 20,000 dalton.

7. The polymer composition according to claim 1 in which the hydrophobic polymer P1 and the hydrophilic polymer P2 are employed in a weight ratio P1:P2 in the range from 1:4 to 2.2:1.

8. The polymer composition of claim 1, wherein said monomers M1a are selected from the group consisting of the esters of acrylic acid with $C_2$-$C_{10}$-alkanols and the esters of methacrylic acid with $C_{1-10}$-alkanols, and wherein said monomers M1b are selected from the group consisting of vinylaromatic monomers, $C_{11}$-$C_{20}$-alkyl acrylates and $C_{11}$-$C_{20}$-alkyl methacrylates.

9. An active compound composition comprising at least one active compound and/or effect substance having a solubility in water at 25° C./1013 mbar of less than 10 g/l and at least one amphiphilic polymer composition according to claim 1.

10. The active compound composition according to claim 9 comprising the active compound and/or effect substance and the amphiphilic polymer composition in a weight ratio of from 1:10 to 3:1.

11. The active compound composition according to claim 9 having a content of volatile organic compounds of less than 10% by weight, based on the total weight of the composition.

12. An aqueous active compound composition comprising an aqueous medium as continuous phase and at least one disperse phase comprising at least one active compound and/or effect substance having a solubility in water at 25° C./1013 bar of less than 10 g/l and at least one amphiphilic polymer composition according to claim 1.

13. The active compound composition according to claim 12 where the particles of the disperse phase have a mean particle size, determined by dynamic light scattering, of not more than 300 nm.

14. The active compound composition according to claim 13 comprising the active compound and/or effect substance and the amphiphilic polymer composition in a weight ratio of from 1:10 to 3:1.

15. The active compound composition according to claim 12 comprising the active compound and/or effect substance and the amphiphilic polymer composition in a weight ratio of from 1:10 to 3:1.

16. A process for preparing an amphiphilic polymer composition according to claim 1, which process comprises reacting i) at least one hydrophobic polymer P1 which is constructed of ethylenically unsaturated monomers M1 and which carries functional groups $R^{P1}$ reactive toward isocyanate groups, and ii) at least one hydrophilic polymer P2 which carries functional groups $R^{P2}$ reactive toward isocyanate groups with iii) at least one compound V which contains isocyanate groups and, with respect to the isocyanate groups, has a functionality of at least 1.5.

17. The process according to claim 16 in which the polymer P1 and the polymer P2 are reacted successively with the compound V.

18. The process according to claim 16 in which the polymer P1 and the polymer P2 are reacted in one step with the compound V.

19. A process for preparing an active compound composition comprising at least one active compound and/or effect substance having a solubility in water at 25° C./1013 mbar of less than 10 g/l and at least one amphiphilic polymer composition according to claim 1 which comprises preparing a homogeneous non-aqueous mixture comprising the amphiphilic polymer composition and at least one active compound and/or effect substance.

20. A process for preparing an aqueous active compound composition comprising an aqueous medium as continuous phase and at least one disperse phase comprising at least one active compound and/or effect substance having a solubility in water at 25° C./1013 bar of less than 10 g/l and at least one amphiphilic polymer composition according to claim 1, which process comprises:

a) preparing a homogeneous nonaqueous mixture comprising amphiphilic polymer composition and active compound and/or effect substance, and b) dispersing the resulting mixture with water.

21. A process for preparing an aqueous active compound composition comprising an aqueous medium as continuous phase and at least one disperse phase comprising at least one active compound and/or effect substance having a solubility in water at 25° C./1013 bar of less than 10 g/l and at least one amphiphilic polymer composition according to claim 1, which process comprises:

a) preparing a solution of active compound and/or effect substance and, if appropriate, amphiphilic polymer composition in an organic solvent having a boiling point below that of water and b) mixing the solution of the active compound and/or effect substance with water or an aqueous solution of the amphiphilic copolymer and c) removing the organic solvent.

22. A process for preparing an aqueous active compound composition comprising an aqueous medium as continuous phase and at least one disperse phase comprising at least one active compound and/or effect substance having a solubility in water at 25° C./1013 bar of less than 10 g/l and at least one amphiphilic polymer composition according to claim 1, which process comprises incorporating the active compound and/or the effect substance into an aqueous solution of the amphiphilic polymer composition, at a temperature above the melting point of the active compound.

* * * * *